United States Patent
Smith

(10) Patent No.: US 8,834,514 B2
(45) Date of Patent: Sep. 16, 2014

(54) RESILIENT BAND MEDICAL DEVICE

(71) Applicant: Xennovate Medical LLC, Richmomd, IN (US)

(72) Inventor: David William Smith, Richmond, IN (US)

(73) Assignee: Xennovate Medical LLC

( * ) Notice: Subject to any disclaimer, the term of this patent is extended or adjusted under 35 U.S.C. 154(b) by 0 days.

(21) Appl. No.: 13/894,941

(22) Filed: May 15, 2013

(65) Prior Publication Data

US 2013/0231698 A1    Sep. 5, 2013

Related U.S. Application Data

(63) Continuation of application No. 11/848,132, filed on Aug. 30, 2007, now abandoned.

(60) Provisional application No. 60/841,403, filed on Aug. 30, 2006.

(51) Int. Cl.
*A61M 29/00* (2006.01)
*B29C 47/00* (2006.01)
(Continued)

(52) U.S. Cl.
CPC .............. *A61F 5/08* (2013.01); *B29C 47/0038* (2013.01); *B29C 47/065* (2013.01); *B29C 47/0054* (2013.01); *B29C 47/0069* (2013.01); *B29C 47/0066* (2013.01); *B29L 2031/753* (2013.01); *B29C 43/222* (2013.01); *B29C 47/0064* (2013.01); *A61M 29/00* (2013.01); *B29C 47/0021* (2013.01); *B29C 59/04* (2013.01); *B29K 2995/0082* (2013.01); *B29C 47/0019* (2013.01); *B29C 47/0033* (2013.01)
USPC .......................................... 606/199

(58) Field of Classification Search
USPC ...................... 606/199; 128/200.24
See application file for complete search history.

(56) References Cited

U.S. PATENT DOCUMENTS

| 1,292,083 A | 1/1919 | Sawyer |
| 2,471,088 A | 5/1949 | Ayre |

(Continued)

FOREIGN PATENT DOCUMENTS

| EM | 001220826-0001 | 8/2010 |
| EM | 001220826-0002 | 8/2010 |

(Continued)

OTHER PUBLICATIONS

CNS, Inc., package insert for Breathe Right® Snore Relief™ product, 2006, 1 page.

(Continued)

*Primary Examiner* — Victor Nguyen
*Assistant Examiner* — Kevin Everage
(74) *Attorney, Agent, or Firm* — Marshall, Gerstein & Borun LLP

(57) ABSTRACT

A medical device includes a one-piece resiliently biased band of base material having opposite first and second side surfaces and an adhesive material for temporarily adhesively securing the band to a user's skin. The band can include a longitudinal axis and a lateral axis that intersects the longitudinal axis. Moreover, the band can include first and second lateral portions disposed on opposite sides of the lateral axis. The lateral portions are mirror images of each other such that the band is symmetrical relative to the lateral axis. Each of the lateral portions include a central portion and first and second extending portions spaced apart from each other on opposite sides of the longitudinal axis of the band and extending away from the central portion. Each of the extending portions further include a perimeter edge defining a portion of an edge of the medical device.

16 Claims, 26 Drawing Sheets

(51) Int. Cl.
*A61F 5/08* (2006.01)
*B29C 43/22* (2006.01)
*B29C 59/04* (2006.01)
B29C 47/06 (2006.01)
B29L 31/00 (2006.01)

(56) References Cited

U.S. PATENT DOCUMENTS

| | | |
|---|---|---|
| 2,498,338 A | 2/1950 | Martin |
| 2,736,721 A | 2/1956 | Dexter |
| 2,814,601 A | 11/1957 | Currie et al. |
| 2,857,356 A | 10/1958 | Goodwin |
| 3,045,047 A | 7/1962 | Davidson et al. |
| D196,412 S | 9/1963 | Ayre |
| D210,757 S | 4/1968 | Michel |
| 3,426,011 A | 2/1969 | Parmerter et al. |
| 3,453,257 A | 7/1969 | Parmerter et al. |
| 3,453,258 A | 7/1969 | Parmerter et al. |
| 3,453,259 A | 7/1969 | Parmerter et al. |
| 3,453,260 A | 7/1969 | Parmerter et al. |
| 3,459,731 A | 8/1969 | Gramera et al. |
| 3,464,413 A | 9/1969 | Goldfarb et al. |
| 3,553,191 A | 1/1971 | Parmerter et al. |
| 3,565,887 A | 2/1971 | Parmerter et al. |
| 3,567,118 A | 3/1971 | Shepherd et al. |
| 3,627,851 A | 12/1971 | Brady |
| 3,645,835 A | 2/1972 | Hodgson |
| 3,655,129 A | 4/1972 | Seiner |
| 3,688,985 A | 9/1972 | Engel et al. |
| 3,710,799 A | 1/1973 | Caballero |
| 3,772,247 A | 11/1973 | Flannigan |
| 3,846,404 A | 11/1974 | Nichols |
| 3,906,073 A | 9/1975 | Kim et al. |
| 3,909,444 A | 9/1975 | Anderson et al. |
| 3,921,636 A | 11/1975 | Zaffaroni |
| 3,948,254 A | 4/1976 | Zaffaroni |
| 3,954,963 A | 5/1976 | Kuderna, Jr. |
| 3,965,033 A | 6/1976 | Matsukawa et al. |
| 3,985,298 A | 10/1976 | Nichols |
| 3,993,072 A | 11/1976 | Zaffaroni |
| 3,994,439 A | 11/1976 | Van Breen et al. |
| 4,016,254 A | 4/1977 | Seager |
| 4,067,824 A | 1/1978 | Teng et al. |
| 4,075,379 A | 2/1978 | Lloyd |
| 4,101,358 A | 7/1978 | Kim et al. |
| 4,128,507 A | 12/1978 | Mitzner |
| 4,136,163 A | 1/1979 | Watson et al. |
| 4,136,250 A | 1/1979 | Mueller et al. |
| 4,145,184 A | 3/1979 | Brain et al. |
| 4,152,272 A | 5/1979 | Young |
| 4,209,417 A | 6/1980 | Whyte |
| 4,230,688 A | 10/1980 | Rowsell et al. |
| 4,243,224 A | 1/1981 | Spector |
| 4,267,831 A | 5/1981 | Aguilar |
| 4,339,356 A | 7/1982 | Whyte |
| 4,356,115 A | 10/1982 | Shibanai et al. |
| 4,386,135 A | 5/1983 | Campbell et al. |
| 4,414,977 A | 11/1983 | Rezakhany |
| 4,422,650 A | 12/1983 | Reinsma et al. |
| 4,427,737 A | 1/1984 | Cilento et al. |
| 4,439,425 A | 3/1984 | Tarcsay et al. |
| 4,487,801 A | 12/1984 | Turnbull et al. |
| 4,492,644 A | 1/1985 | Matsumoto et al. |
| 4,493,869 A | 1/1985 | Sweeny et al. |
| 4,515,705 A | 5/1985 | Moeddel |
| 4,523,589 A | 6/1985 | Krauser |
| 4,528,226 A | 7/1985 | Sweeny |
| 4,535,152 A | 8/1985 | Szejtli et al. |
| 4,576,168 A | 3/1986 | Jalowayski |
| 4,582,492 A | 4/1986 | Etter et al. |
| 4,597,959 A | 7/1986 | Barr |
| 4,616,008 A | 10/1986 | Hirai et al. |
| 4,633,863 A | 1/1987 | Filips et al. |
| 4,638,043 A | 1/1987 | Szycher et al. |
| 4,638,058 A | 1/1987 | Brandt et al. |
| 4,654,256 A | 3/1987 | Doree et al. |
| 4,655,767 A | 4/1987 | Woodard et al. |
| 4,661,388 A | 4/1987 | Charbonneau |
| 4,675,009 A | 6/1987 | Hymes et al. |
| 4,678,598 A | 7/1987 | Ogino et al. |
| 4,693,858 A | 9/1987 | Volke |
| 4,720,417 A | 1/1988 | Sweeny et al. |
| 4,732,146 A | 3/1988 | Fasline et al. |
| 4,738,984 A | 4/1988 | Parker |
| 4,743,499 A | 5/1988 | Volke |
| 4,746,734 A | 5/1988 | Tsuchiyama et al. |
| 4,774,133 A | 9/1988 | Doree et al. |
| 4,802,626 A | 2/1989 | Forbes et al. |
| 4,808,466 A | 2/1989 | Kotani et al. |
| 4,826,683 A | 5/1989 | Bates |
| 4,827,925 A | 5/1989 | Vilasi |
| 4,842,761 A | 6/1989 | Rutherford |
| 4,867,150 A | 9/1989 | Gilbert |
| 4,880,690 A | 11/1989 | Szycher et al. |
| 4,880,851 A | 11/1989 | Yamamoto |
| 4,889,755 A | 12/1989 | Charbonneau |
| 4,898,633 A | 2/1990 | Doree et al. |
| 4,899,739 A | 2/1990 | Konishi |
| 4,925,517 A | 5/1990 | Charbonneau et al. |
| 4,927,631 A | 5/1990 | Bates |
| 4,942,714 A | 7/1990 | Langley, Jr. et al. |
| 4,951,657 A | 8/1990 | Pfister et al. |
| 4,952,400 A | 8/1990 | Tararuj et al. |
| D310,565 S | 9/1990 | Petruson |
| 4,970,240 A | 11/1990 | Kielley |
| 4,971,798 A | 11/1990 | Coia et al. |
| 4,988,577 A | 1/1991 | Jamieson |
| 5,000,486 A | 3/1991 | Rua, Jr. et al. |
| 5,018,974 A | 5/1991 | Carnahan et al. |
| 5,022,389 A | 6/1991 | Brennan |
| 5,035,886 A | 7/1991 | Chakrabarti et al. |
| 5,043,161 A | 8/1991 | Scarpelli et al. |
| 5,071,645 A | 12/1991 | Johnson et al. |
| 5,071,704 A | 12/1991 | Fischel-Ghodsian |
| 5,081,104 A | 1/1992 | Orson, Sr. |
| 5,090,408 A | 2/1992 | Spofford et al. |
| 5,114,735 A | 5/1992 | Rua, Jr. et al. |
| 5,114,979 A | 5/1992 | Kielley |
| 5,124,162 A | 6/1992 | Boskovic et al. |
| 5,175,152 A | 12/1992 | Singh |
| 5,186,168 A | 2/1993 | Spofford et al. |
| 5,198,226 A | 3/1993 | MacFarlane et al. |
| 5,209,801 A | 5/1993 | Smith |
| 5,223,251 A | 6/1993 | Nichols |
| 5,232,702 A | 8/1993 | Pfister et al. |
| 5,232,769 A | 8/1993 | Yamato et al. |
| 5,234,610 A | 8/1993 | Gardlik et al. |
| 5,269,769 A | 12/1993 | Dhara et al. |
| 5,288,492 A | 2/1994 | Morris |
| 5,297,546 A | 3/1994 | Spofford et al. |
| 5,303,917 A | 4/1994 | Uke |
| 5,322,689 A | 6/1994 | Hughes et al. |
| 5,336,665 A | 8/1994 | Garner-Gray et al. |
| 5,378,468 A | 1/1995 | Suffis et al. |
| 5,380,707 A | 1/1995 | Barr et al. |
| 5,383,891 A | 1/1995 | Walker |
| 5,391,374 A | 2/1995 | Charbonneau et al. |
| 5,392,568 A | 2/1995 | Howard, Jr. et al. |
| 5,395,047 A | 3/1995 | Pendergrass, Jr. |
| 5,455,043 A | 10/1995 | Fischel-Ghodsian |
| 5,459,157 A | 10/1995 | Stroppolo et al. |
| 5,466,724 A | 11/1995 | Volke et al. |
| 5,476,091 A | 12/1995 | Johnson |
| 5,478,565 A | 12/1995 | Geria |
| 5,479,944 A | 1/1996 | Petruson |
| 5,496,813 A | 3/1996 | Eugster et al. |
| 5,500,154 A | 3/1996 | Bacon et al. |
| 5,508,259 A | 4/1996 | Holzner et al. |
| 5,530,989 A | 7/1996 | Remmert et al. |
| 5,533,499 A | 7/1996 | Johnson |
| 5,533,503 A | 7/1996 | Doubek et al. |
| 5,534,561 A | 7/1996 | Volke |
| 5,536,263 A | 7/1996 | Rolf et al. |
| 5,538,500 A | 7/1996 | Peterson |

(56) References Cited

U.S. PATENT DOCUMENTS

| | | |
|---|---|---|
| 5,546,929 A | 8/1996 | Muchin |
| 5,549,103 A | 8/1996 | Johnson |
| 5,553,605 A | 9/1996 | Muchin |
| 5,562,908 A | 10/1996 | Geria |
| 5,569,218 A | 10/1996 | Berg |
| 5,569,679 A | 10/1996 | Jacob |
| 5,570,689 A | 11/1996 | Starr et al. |
| RE35,408 E | 12/1996 | Petruson |
| 5,585,343 A | 12/1996 | McGee et al. |
| 5,605,543 A | 2/1997 | Swanson |
| 5,611,333 A * | 3/1997 | Johnson .................. 128/200.24 |
| 5,611,334 A | 3/1997 | Muchin |
| 5,622,992 A | 4/1997 | Beck |
| D379,513 S | 5/1997 | Ierulli |
| 5,626,552 A | 5/1997 | Nomura et al. |
| 5,626,852 A | 5/1997 | Suffis et al. |
| D380,264 S | 6/1997 | Petruson |
| 5,653,224 A | 8/1997 | Johnson |
| 5,665,104 A | 9/1997 | Lee |
| 5,669,377 A | 9/1997 | Fenn |
| 5,681,577 A | 10/1997 | Lech et al. |
| 5,685,292 A | 11/1997 | Fenn |
| 5,686,105 A | 11/1997 | Kelm et al. |
| D388,172 S | 12/1997 | Cipes |
| 5,706,800 A | 1/1998 | Cronk et al. |
| 5,711,941 A | 1/1998 | Behan et al. |
| 5,718,224 A | 2/1998 | Muchin |
| 5,720,966 A | 2/1998 | Ostendorf |
| 5,723,420 A | 3/1998 | Wei et al. |
| 5,725,865 A | 3/1998 | Mane et al. |
| 5,727,544 A | 3/1998 | Miura |
| 5,735,272 A | 4/1998 | Dillon et al. |
| 5,740,798 A | 4/1998 | McKinney |
| 5,741,510 A | 4/1998 | Rolf et al. |
| 5,743,876 A | 4/1998 | Swanson |
| 5,746,770 A | 5/1998 | Zeitels et al. |
| 5,752,511 A | 5/1998 | Simmons et al. |
| 5,842,469 A | 12/1998 | Rapp et al. |
| 5,890,486 A | 4/1999 | Mitra et al. |
| 5,897,537 A | 4/1999 | Berg et al. |
| 5,911,715 A | 6/1999 | Berg et al. |
| 5,957,126 A | 9/1999 | Neeser |
| 5,961,537 A | 10/1999 | Gould |
| 6,029,658 A | 2/2000 | De Voss |
| D422,358 S | 4/2000 | Lundy, Jr. et al. |
| D422,702 S | 4/2000 | Lundy, Jr. et al. |
| D422,703 S | 4/2000 | Lundy, Jr. et al. |
| 6,065,470 A | 5/2000 | Van Cromvoirt et al. |
| 6,090,403 A | 7/2000 | Block et al. |
| 6,092,521 A | 7/2000 | Miura |
| D429,332 S | 8/2000 | Ierulli |
| D430,295 S | 8/2000 | Ierulli |
| 6,098,616 A | 8/2000 | Lundy, Jr. et al. |
| 6,123,082 A | 9/2000 | Berthon-Jones |
| D432,652 S | 10/2000 | Ierulli |
| 6,183,770 B1 | 2/2001 | Muchin et al. |
| D441,081 S | 4/2001 | Mueller |
| 6,213,121 B1 | 4/2001 | Cardarelli |
| 6,244,265 B1 | 6/2001 | Cronk et al. |
| 6,248,247 B1 | 6/2001 | Goenka et al. |
| 6,261,593 B1 | 7/2001 | Muchin et al. |
| 6,270,831 B2 | 8/2001 | Kumar et al. |
| 6,276,360 B1 | 8/2001 | Cronk et al. |
| 6,295,982 B1 | 10/2001 | Reed, Jr. |
| 6,318,362 B1 | 11/2001 | Johnson |
| 6,352,548 B1 | 3/2002 | Blach et al. |
| 6,399,192 B1 | 6/2002 | Pinna et al. |
| 6,453,901 B1 | 9/2002 | Ierulli |
| 6,463,633 B1 | 10/2002 | Sangani et al. |
| 6,475,703 B2 | 11/2002 | Li et al. |
| 6,550,474 B1 | 4/2003 | Anderson et al. |
| 6,569,934 B2 | 5/2003 | Noel, III |
| 6,631,714 B2 | 10/2003 | Von Duyke et al. |
| 6,645,338 B1 | 11/2003 | Sangani et al. |
| 6,678,553 B2 | 1/2004 | Lerner et al. |
| D490,897 S | 6/2004 | Ruch |
| 6,767,202 B2 | 7/2004 | Gorman et al. |
| 6,769,428 B2 | 8/2004 | Cronk et al. |
| 6,769,429 B1 | 8/2004 | Benetti |
| 6,823,864 B2 | 11/2004 | Blach et al. |
| 6,858,024 B1 | 2/2005 | Berg et al. |
| 6,902,575 B2 | 6/2005 | Laakso et al. |
| 6,969,479 B2 | 11/2005 | Gorman et al. |
| 7,007,696 B2 | 3/2006 | Palkon et al. |
| 7,011,093 B2 | 3/2006 | Anderson et al. |
| 7,013,889 B2 | 3/2006 | Cronk et al. |
| 7,017,580 B2 | 3/2006 | Prescott et al. |
| 7,037,457 B2 | 5/2006 | Seidel et al. |
| 7,067,710 B1 | 6/2006 | Beaudry |
| 7,114,495 B2 | 10/2006 | Lockwood, Jr. |
| 7,118,545 B2 | 10/2006 | Boyde |
| D574,085 S | 7/2008 | Lucchetti |
| D639,762 S | 6/2011 | Brogden et al. |
| D644,324 S | 8/2011 | Brunner et al. |
| D644,325 S | 8/2011 | Brunner et al. |
| 8,047,201 B2 | 11/2011 | Guyuron et al. |
| D651,710 S | 1/2012 | Brogden et al. |
| D659,245 S | 5/2012 | Ierulli |
| D662,203 S | 6/2012 | Smith |
| 8,313,508 B2 | 11/2012 | Belson et al. |
| D672,461 S | 12/2012 | Brogden et al. |
| D673,270 S | 12/2012 | Brunner et al. |
| 2001/0002000 A1 | 5/2001 | Kumar et al. |
| 2001/0032645 A1 | 10/2001 | Cronk et al. |
| 2002/0000227 A1 | 1/2002 | Duyke et al. |
| 2002/0086243 A1 | 7/2002 | Li et al. |
| 2003/0114910 A1 | 6/2003 | Juhani Laakso et al. |
| 2004/0005830 A1 | 1/2004 | Anderson et al. |
| 2004/0149290 A1 | 8/2004 | Nelson et al. |
| 2004/0231679 A1 | 11/2004 | Prescott et al. |
| 2004/0242976 A1 | 12/2004 | Abreu |
| 2004/0243102 A1 | 12/2004 | Berg et al. |
| 2005/0045188 A1 | 3/2005 | Mendius et al. |
| 2005/0066965 A1* | 3/2005 | Cronk et al. ............. 128/200.24 |
| 2005/0081846 A1 | 4/2005 | Barney |
| 2005/0124445 A1 | 6/2005 | Veilleux et al. |
| 2005/0129913 A1 | 6/2005 | Kobayashi et al. |
| 2005/0149158 A1 | 7/2005 | Hunter et al. |
| 2005/0161046 A1 | 7/2005 | Michaels |
| 2005/0165488 A1 | 7/2005 | Hunter et al. |
| 2005/0175663 A1 | 8/2005 | Hunter et al. |
| 2005/0175665 A1 | 8/2005 | Hunter et al. |
| 2005/0175703 A1 | 8/2005 | Hunter et al. |
| 2005/0177225 A1 | 8/2005 | Hunter et al. |
| 2005/0178395 A1 | 8/2005 | Hunter et al. |
| 2005/0181008 A1 | 8/2005 | Hunter et al. |
| 2005/0181011 A1 | 8/2005 | Hunter et al. |
| 2005/0189372 A1 | 9/2005 | Fenton |
| 2005/0244614 A1 | 11/2005 | Bharadwaj et al. |
| 2005/0284485 A9 | 12/2005 | Nelson et al. |
| 2006/0085027 A1 | 4/2006 | Santin et al. |
| 2007/0012350 A1 | 1/2007 | Kim et al. |
| 2007/0255309 A1 | 11/2007 | Guyuron et al. |
| 2008/0058858 A1 | 3/2008 | Smith |
| 2008/0097517 A1 | 4/2008 | Holmes et al. |
| 2008/0184995 A1 | 8/2008 | Ierulli |
| 2008/0257341 A1 | 10/2008 | Ierulli |
| 2009/0234383 A1 | 9/2009 | Ierulli |
| 2011/0000483 A1 | 1/2011 | Matthias et al. |
| 2011/0027353 A1 | 2/2011 | Cronk et al. |
| 2011/0093004 A1 | 4/2011 | Ierulli |
| 2012/0172923 A1 | 7/2012 | Fenton et al. |

FOREIGN PATENT DOCUMENTS

| | | |
|---|---|---|
| EM | 001220826-0003 | 8/2010 |
| EM | 001220826-0004 | 8/2010 |
| EP | 195254 | 9/1986 |
| EP | 0588949 | 3/1994 |
| EP | 0659522 | 6/1995 |
| EP | 0799114 | 10/1997 |
| EP | 0820743 A2 | 1/1998 |
| EP | 0820744 | 1/1998 |
| EP | 0820745 | 1/1998 |

(56) References Cited

FOREIGN PATENT DOCUMENTS

| | | |
|---|---|---|
| EP | 0842646 | 5/1998 |
| EP | 0861674 | 9/1998 |
| EP | 0900553 | 3/1999 |
| EP | 0909151 | 4/1999 |
| EP | 0912210 | 5/1999 |
| EP | 1006764 | 6/2000 |
| EP | 1006963 | 6/2000 |
| EP | 1033118 | 9/2000 |
| EP | 1035821 | 9/2000 |
| EP | 1174100 | 1/2002 |
| EP | 1267976 | 1/2003 |
| EP | 1299056 | 4/2003 |
| JP | 03020217 | 1/1991 |
| JP | 04-31518 U | 3/1992 |
| JP | 04131624 U | 12/1992 |
| JP | 06508273 | 9/1994 |
| JP | 07048250 | 2/1995 |
| JP | 3012542 U | 6/1995 |
| JP | 07215847 | 8/1995 |
| JP | 07268383 | 10/1995 |
| JP | 07303829 | 11/1995 |
| JP | 08208429 | 8/1996 |
| JP | 3034804 U | 12/1996 |
| JP | 3034806 U | 12/1996 |
| JP | 10120555 | 5/1998 |
| WO | WO-91/01801 | 2/1991 |
| WO | WO-92/14607 | 9/1992 |
| WO | WO-92/22340 | 12/1992 |
| WO | WO-93/13938 | 7/1993 |
| WO | WO-93/24161 | 12/1993 |
| WO | WO-95/04542 | 2/1995 |
| WO | WO-95/21640 | 8/1995 |
| WO | WO-95/24236 | 9/1995 |
| WO | WO-95/26155 | 10/1995 |
| WO | WO-96/10413 | 4/1996 |
| WO | WO-96/39524 | 12/1996 |
| WO | WO-96/40070 | 12/1996 |
| WO | WO-97/18801 | 5/1997 |
| WO | WO-97/38651 | 10/1997 |
| WO | WO-97/46275 | 12/1997 |
| WO | WO-98/06360 | 2/1998 |
| WO | WO-98/27897 | 7/1998 |
| WO | WO-98/32403 | 7/1998 |
| WO | WO-98/57613 | 12/1998 |
| WO | WO-99/22678 | 5/1999 |
| WO | WO-99/27880 | 6/1999 |
| WO | WO-99/36193 | 7/1999 |
| WO | WO-01/74432 | 10/2001 |
| WO | WO-01/96457 | 12/2001 |
| WO | WO-02/05734 | 1/2002 |
| WO | WO-02/15896 | 2/2002 |
| WO | WO-03/051235 | 6/2003 |
| WO | WO-03/060843 | 7/2003 |
| WO | WO-2004/108817 | 12/2004 |
| WO | WO-2005/015163 | 2/2005 |
| WO | WO-2005/020845 | 3/2005 |
| WO | WO-2005/051292 | 6/2005 |
| WO | WO-2005/063328 | 7/2005 |

OTHER PUBLICATIONS

European Search Report for EP 07 84 1675 dated Oct. 8, 2009.
International Search Report and Written Opinion for PCT/US2007/077313 dated Apr. 1, 2008, 6 pages.
Kienstra et al., "Effects of the Nasal Muscles on the Nasal Airway," American Jornal of Rhinology, 19:4, Jul.-Aug. 2005.

* cited by examiner

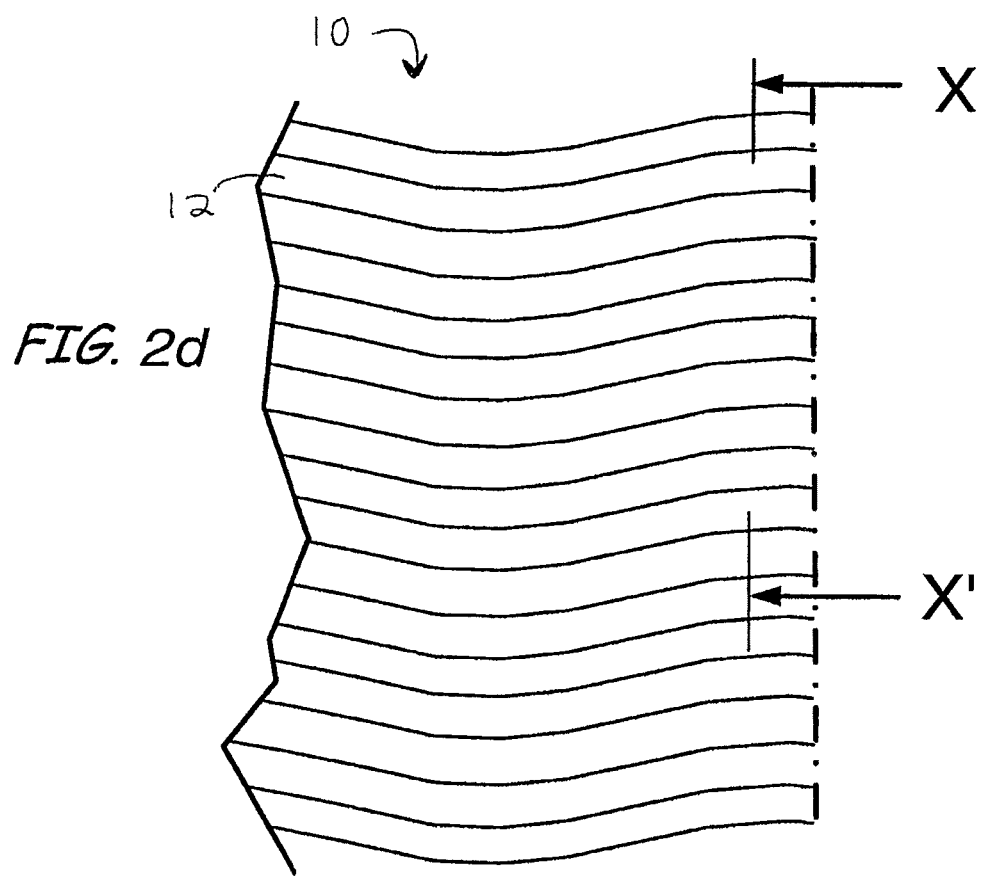

RESILIENT BAND MEDICAL DEVICE

CROSS-REFERENCE TO RELATED APPLICATIONS

This is a continuation of U.S. patent application Ser. No. 11/848,132, filed Aug. 30, 2007, which claims priority to U.S. Provisional Application No. 60/841,403, filed on Aug. 30, 2006, the entire contents of each of which are hereby incorporated herein by reference.

BACKGROUND

The materials manufacturing industry has been extruding plastic polymer sheeting materials for many years. Such extrusion has included etching steel rollers to imprint a texture, such as a matte finish, onto the plastic sheeting as it is extruded. For example, plastic materials having a "leather-like" finish for automotive interiors are made by imprinting the "leather-like" appearance onto the sheeted polymer material.

More recently, etched or machined rollers have been used to impart more intricate designs, such as a diamond-shaped pattern, onto sheeted plastic materials, such as those used for truck bed liners.

SUMMARY OF THE INVENTION

The present invention is directed to a material having a desired stiffness, said stiffness resulting from a groove or a plurality of grooves or cross sectional shapes imparted onto one or more surfaces of the material. These grooves may be uniformly continuous across the web or may be discontinuous, providing alternating or varying stiffness throughout the web. The present invention is also directed to a method for making the material.

The present invention is also directed to a nasal dilator for dilating nasal passages using the material of the present invention. The material is preferably of sufficient stiffness to lift and dilate the nasal passages when secured to the nose.

The present invention is also directed to medical devices, packaging, or construction materials made from the material described herein.

BRIEF DESCRIPTION OF THE DRAWINGS

FIGS. 2a-e are various views of the grooved material of the present invention.

DETAILED DESCRIPTION

The present invention is directed to the unexpected discovery that imparting a functional, structural change to an extruded polymeric material can result in physical changes to the structural geometry of the polymers, thereby providing the effects of mono-axial or multi-axial orientation to the sheeted material.

Figure 1:
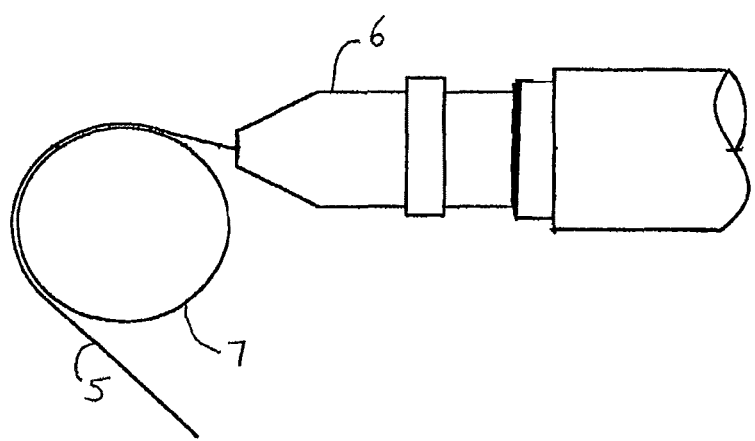
FIG. 1 shows a diagram of conventional polymer sheet extrusion.

Traditionally, bi-axial and mono-axial orientation in a polymeric material have been accomplished by extruding polymers and stretching them as they cool down, which orients the polymers at the molecular level in the direction in which they are stretched (usually the machine processing direction only). Expensive tooling and specialized expertise is often required for this method. A schematic diagram of conventional extrusion is shown in FIG. 1. Polymeric material 5 is pumped through extrusion die assembly 6. As material 5 leaves the die assembly 6, it is cooled on chill or nip roll 7, and then further processed as desired.

The present invention is surprisingly able to achieve the effects of mono-axial orientation in a polymeric material by etching grooves or even discontinuous cross sectional shapes into the polymer sheet or web as it is extruded, rather than by stretching the polymers as they cool. As a result, it is possible to create the effect of molecular reorientation by physical means. Furthermore, by strengthening the material in one direction, the strength is reduced in others, allowing a significant degree of control over the flexural and other properties of the extruded material. In accordance with the present invention, it is possible to create a web of grooved material in which the channels are weakened to a specific degree allow one to tear the web with significantly less force along the channel without tearing outside the channel, resulting in a clean torn edge, substantially without sharp or jagged edges.

As used herein, the term "grooves" shall be used to include furrows or channels (continuous or discontinuous) having any length or width, and any appearance or design from either a top view or a cross-sectional view of the groove. The shape, dimensions and frequency of the grooves are preferably selected to impart a desired stiffness to the material. The desired stiffness can be selected based in part on the type of material being extruded, the thickness of the material, the flexural modulus of the material, and the cross-sectional design or appearance of the grooves or resultant web.

"Flexural modulus", as used herein, shall refer to the ratio, within the elastic limit, of the applied stress on a test specimen in flexure, to the corresponding strain in the outermost fibers of the specimen.

As used herein, "mono-axial orientation" or "multi-axial orientation" shall refer to the process of stretching a hot polymer film or other article in one or more directions under conditions that result in molecular reorientation.

Figure 2A:
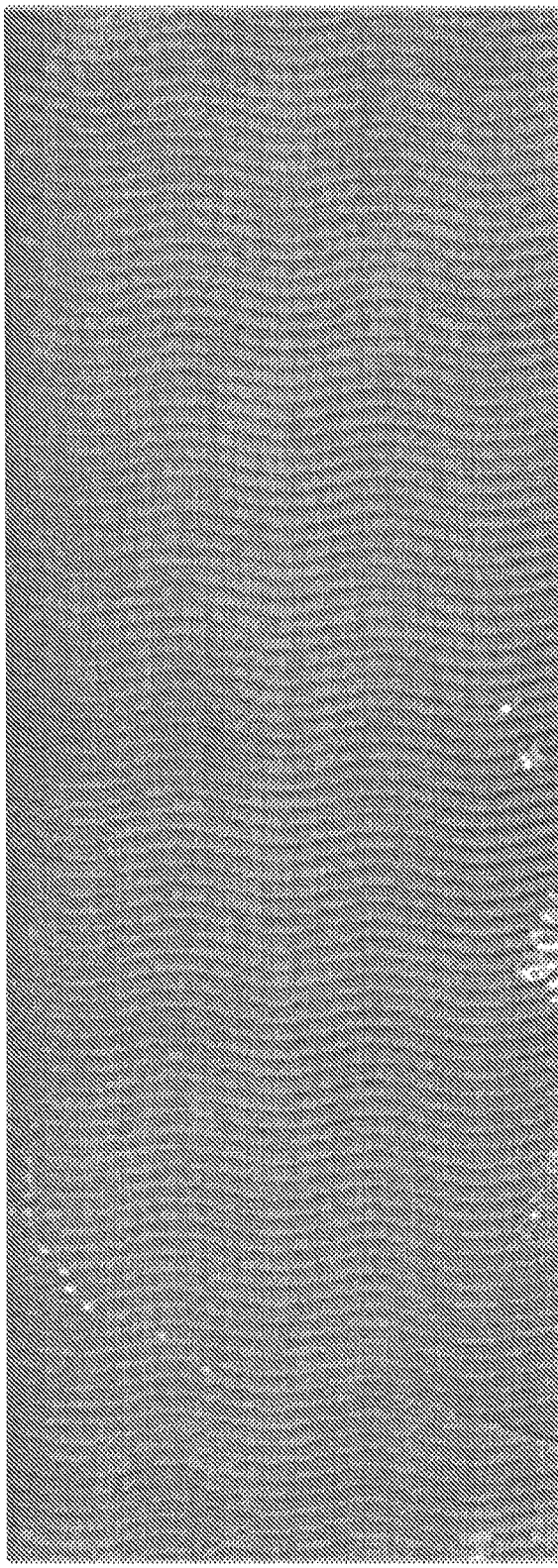
Figure 2B:
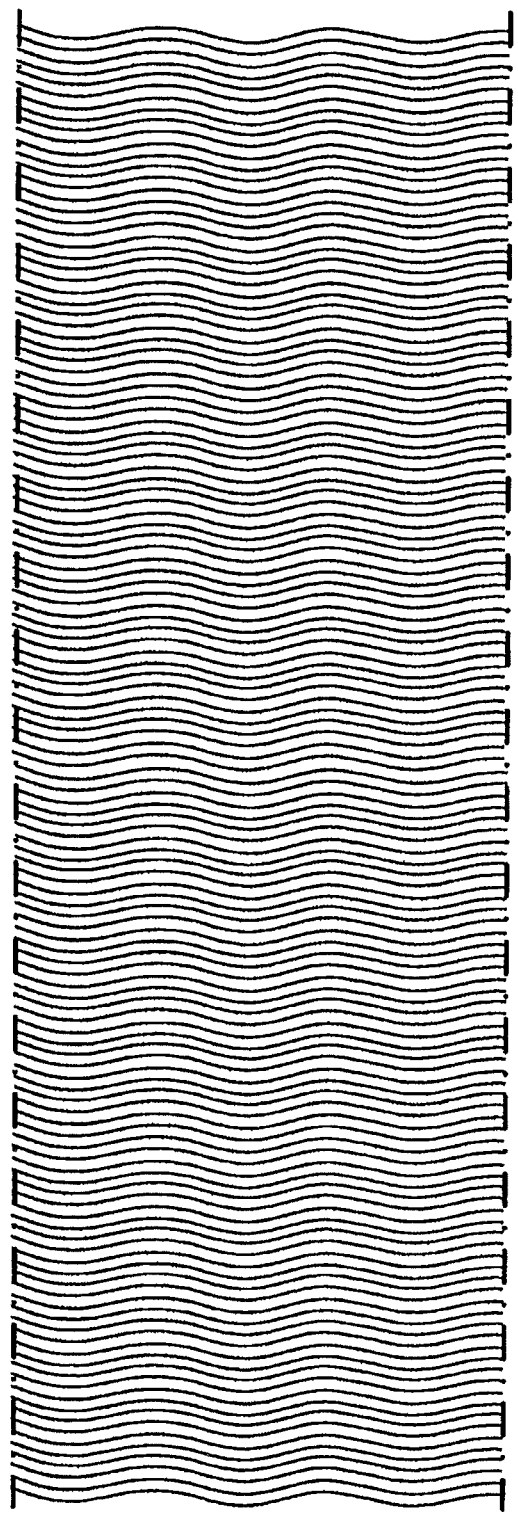
Figure 2C:
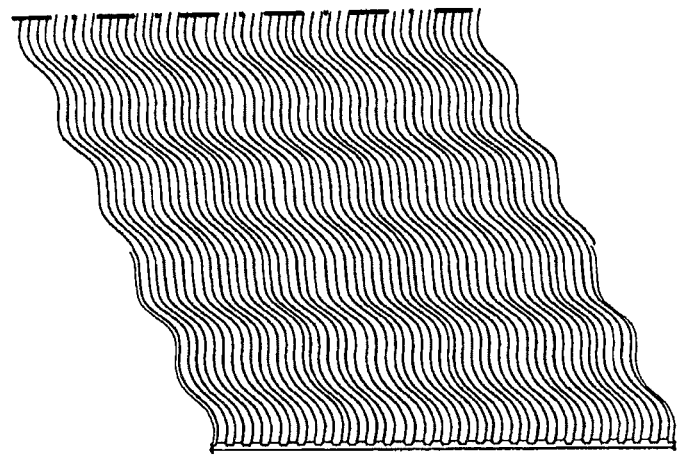
Figure 2E:
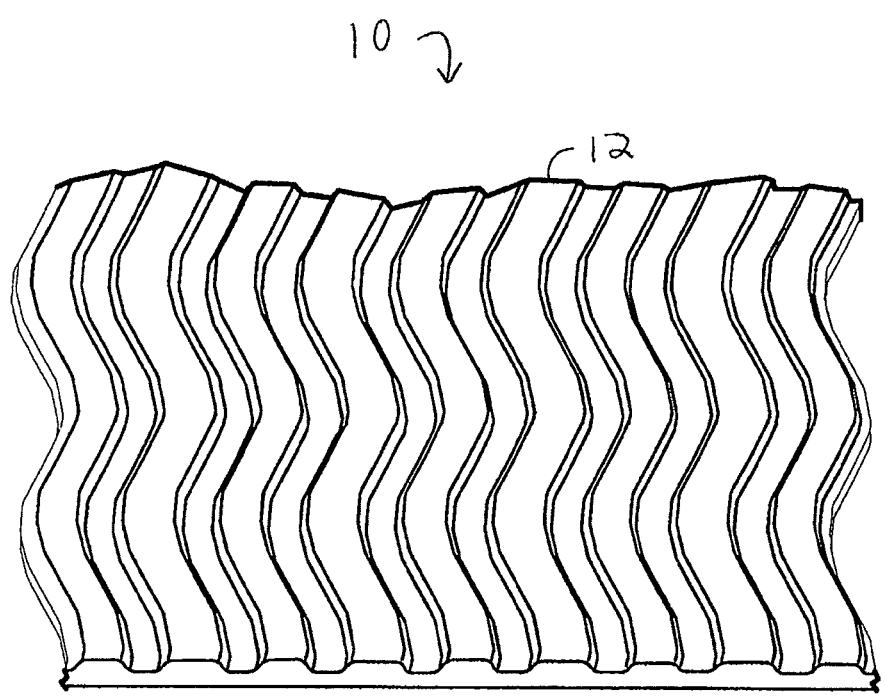
Figure 3A:
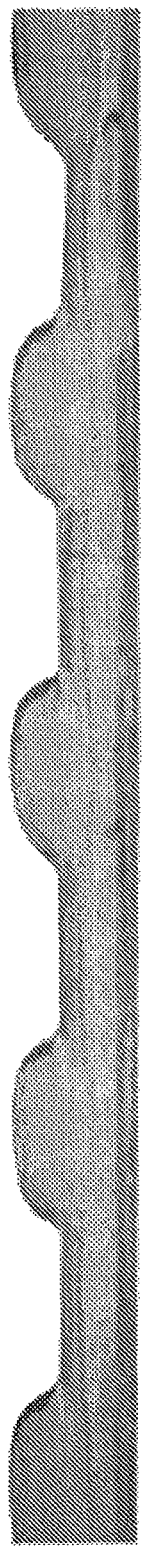
FIGS. 3a and b are cross-sectional views of the grooved material of the present invention.
Figure 3B:
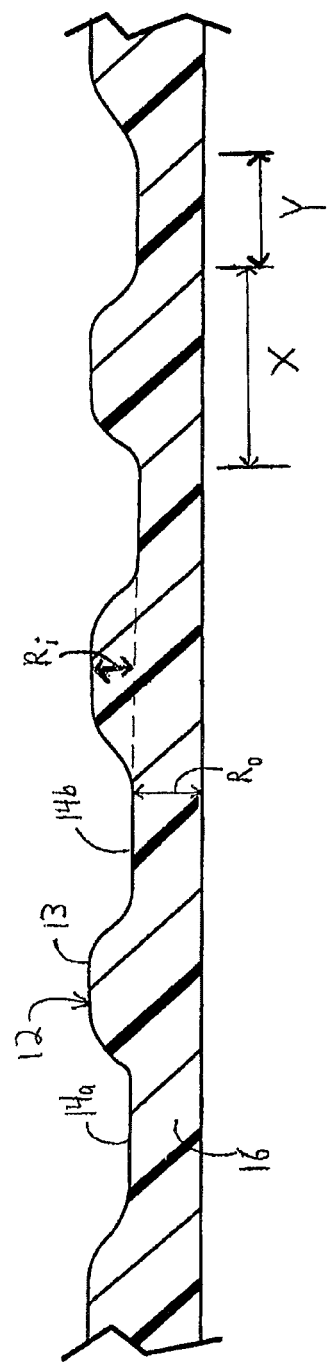

One embodiment of the grooved material of the present invention is shown in FIGS. 2a-e. As best seen in FIG. 2e, the material 10 has at least one groove 12 imparted onto a surface of material 10. FIGS. 3a and b show a cross-sectional view of the material 10, taken along line x-x' of FIG. 2d. As seen in FIGS. 3a and b, groove 12 comprises a ridge 13 having a thickness or height, shown as $R_i$, and a width, shown as "X." Groove 12 further comprises one or more valleys 14, so that each ridge 13 is flanked on at least one side or on both sides by a valley 14, shown as 14a and 14b in FIG. 3b. Valley 14 has a floor or base 16 having a thickness $R_0$, and a width, shown as "Y," of about 0.5.X, although these relative dimensions may vary depending on the degree of stiffness desired.

The widths and heights or thicknesses of the peaks and valleys of the grooves can be calculated to provide an exact stiffness in both the machine processing direction and the transverse direction. For a uniform, flat web of material, the equation is:

$$\text{Stiffness} = (F_m \times T^3)(1/12)$$

where $F_m$ is the flexural modulus of the starting material, and T is the thickness of the material.

The grooves can provide the effects of mono-axial orientation in either the machine or transverse directions. In the embodiment in which grooves are made onto the material in the machine processing direction, thickness (T) is the sum of the peaks of the grooves, plus the thickness of the base of the material, as shown in FIG. 3. In the transverse direction, thickness is that of the base of the material.

Figure 4:
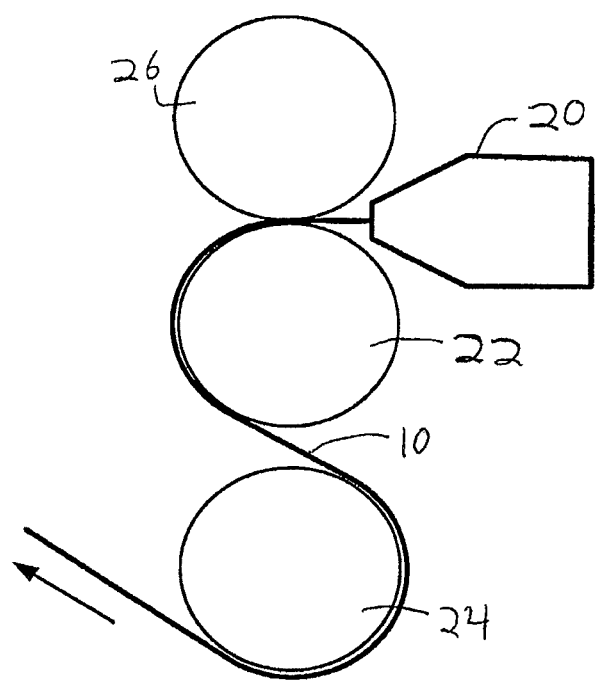
FIG. 4 is a diagram of an extrusion apparatus suitable for extruding the material of the present invention.

The grooves can be imparted onto the material using conventional extrusion technology or any other methods capable of creating grooves, cross sectional shapes or channels in the material, such as by casting, thermoforming or vacuforming the grooves into the material. An example of a suitable extrusion process is shown in FIG. 4. As the material 10 exits the extruder 20, it is fed into nip rollers 22 and 24. In one embodiment of the present invention, nip roller 22 imparts a first texture onto the material, such as grooves. Optionally, a second texture can be imparted onto the material by adding another nip roller 26. The second texture imparted by nip roller 26 can be the same as the first texture, or can be different. The second texture can be imparted in the same processing direction as the first texture, or in a different direction, such as perpendicular to the first texture. In addition to the grooved textures described above, examples of other textures suitable for one or more surfaces of the material include a matte texture, a fabric texture, a leather texture, a combination of textures, and the like.

It is preferred that the nip rollers used to make the grooved material of the present invention are nearly perfectly round, as irregularities may not provide the desired properties achieved by the careful calculations of the groove dimensions. It is preferred that the groove dimensions be imparted to the material with as little deviation from the desired dimensions as possible. If a repeating design, such as a sine wave, is placed in the machine direction, care must be taken to achieve matching of the design onto itself when circumferentially placed around the roll.

The grooves can be imparted in any configuration. In one embodiment, straight grooves are etched into the material. In another embodiment, sinusoidal grooves are etched into the material. The grooves in the embodiments shown in the Figures are imparted in a either in a parallel or sinusoidal pattern. Other patterns, such as, but not limited to, zig-zags, scallops, flutes, and combinations of patterns are also contemplated by the present invention. The patterns may be continuous or discontinuous, and regular or irregular along the material, and may intersect at one or more locations to provide additional strength or stiffness at the point of intersection.

Figure 5A:
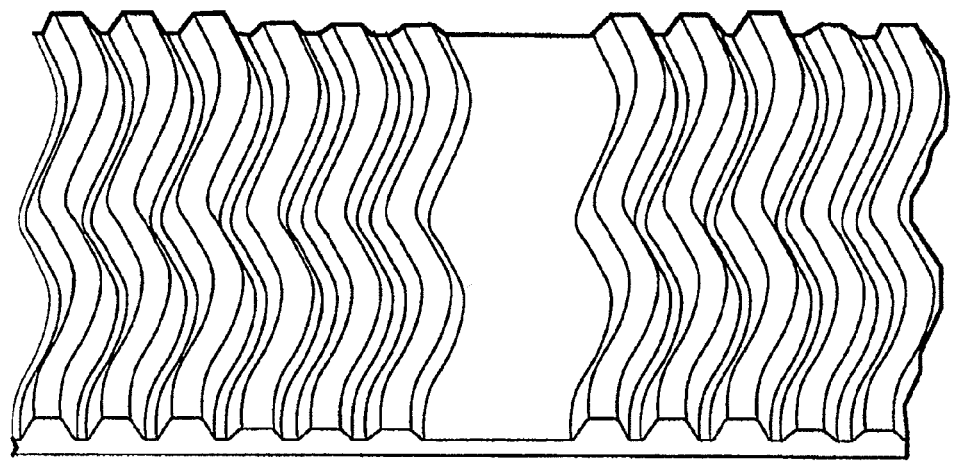
FIGS. 5a and b are various views of another embodiment of the grooved material of the present invention.
Figure 5B:

The configuration of the grooves can also be etched in other designs, such as words, pictures, a raised watermark or a logo. The grooves can have varying thicknesses in the transverse direction, or there can be ungrooved portions between a groove or series of grooves. An example of a material having grooves with varying thicknesses is shown in FIGS. 5a and b.

The grooves, in addition to providing the effects of mono-axial or multi-axial orientation to the material, increase the surface area of the material, and can be used to provide a trough for the application of additional materials, such as, but not limited to adhesives, dyes, medications, fragrances, and the like.

Materials suitable for use in the method of the present invention include any formable material. Such materials include, but are not limited to, thermoplastic polymeric materials like acrylonitrile-butadiene-styrene (ABS), polyethylenes including high density polyethylene (HDPE), low density polyethylene (LDPE) and high molecular weight polyethylene (HMWPE), polypropylene, polyesters including polyethylene terephthalate (PET) and glycolised polyethylene terephthalate (PETG), polystyrene, polyurethane, vinyl, linoleum, rubber compounds, acrylics, nylon compounds, corn derivatives or other biodegradable resins, such as polylactic acid and polyhydroxyalkanoates, combinations of any of the foregoing, and the like.

In addition to the formable materials described above, additional components may be added to the formable material, either before, during or after extrusion. Examples of such components include, but are not limited to, fragrances, medications, homeopathic compositions, aromatherapeutic compositions, antimicrobial agents, adhesives, dyes, pesticides, fungicides, herbicides, and combinations thereof.

Figure 6A:
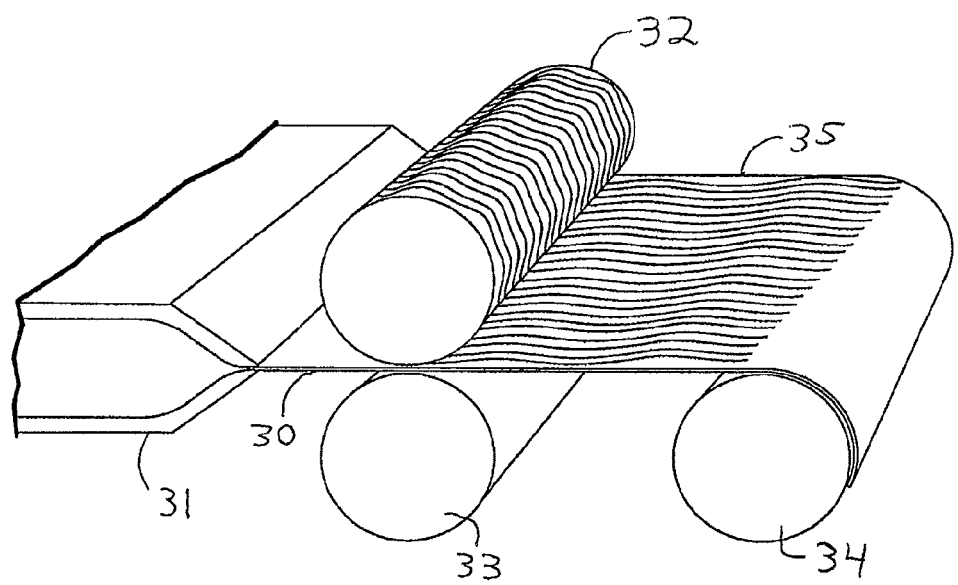
FIG. 6a is a process diagram of grooves being imparted to an extruded material.

FIG. 6a is a process diagram of grooves being imparted to an extruded material. After the material passes through the extrusion die 31, the extruded material 30 passes between an etched nip roller 32 and a matte finish nip roller 33. The etched nip roller 32 imparts grooves to the extruded material 30 by impressing valleys into said material. The resulting grooved material 35 may then be rolled onto a take-up roller 34.

Figure 6B:
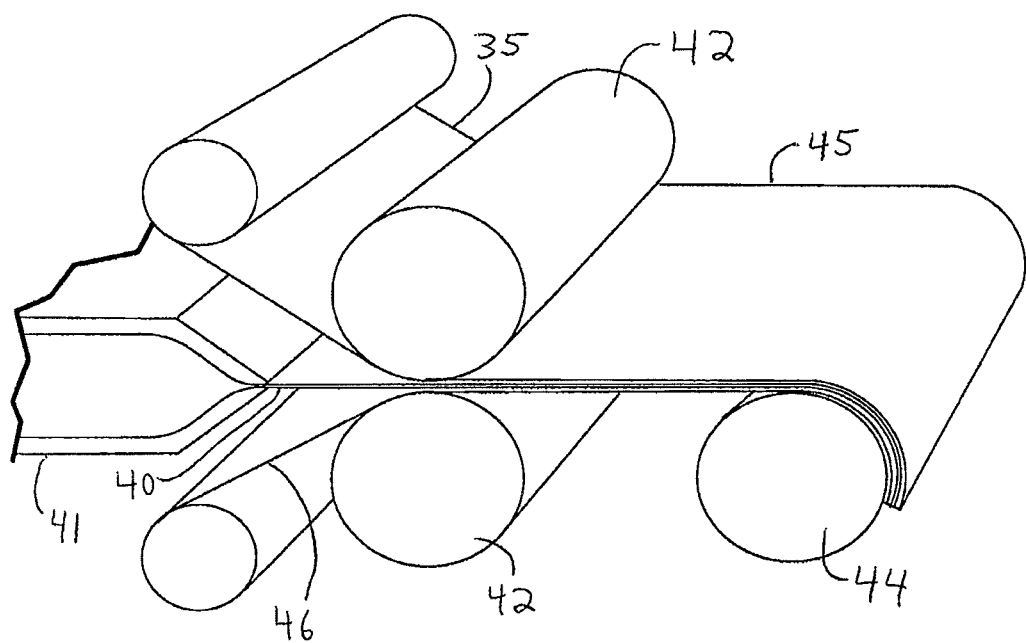
FIG. 6b is a process diagram of an adhesive layer and release liner layer being applied to an extruded grooved material.

After the grooves are imparted to the material, an adhesive layer and release liner layer may be applied to one side of the grooved material. FIG. 6b is a process diagram of an adhesive layer 40 and release liner layer 46 being applied to the extruded grooved material 35. The adhesive material passes through an extrusion die 41, to form adhesive layer 40. Grooved material 35 and release liner layer 46 are positioned on either side of adhesive layer 40. The grooved material 35 is positioned so that the grooved side of the material 35 is facing downward, toward the adhesive layer 40. The grooved material 35, adhesive layer 40, and release liner layer 46 pass between nip rollers 42, to yield a layered product 45. In this layered product 45, the adhesive from the adhesive layer 40 is in contact with and/or embedded within the grooves of the grooved material 35. The layered product 45 may be rolled onto a take-up roller 44.

After the material is extruded and the grooves are imparted, further processing can occur. For example, the grooved material can be cut or stamped into desired shapes, and the cut pieces further processed into the final product. A dye laser can be used to impart a desired image or design onto one or both surfaces of the material.

By using the known flexural modulus of the starting material, the resulting stiffness can be predicted (and adjusted accordingly) to make the desired product. Examples of such products include, but are not limited to, packaging, medical devices and consumer health products, and construction materials. One embodiment of the invention described below is for a nasal dilator.

The present invention can be used to make any type of product in which the stiffness of one or more materials in the product is preferably controlled and/or controllable within a certain degree of flexure. The method can be used to make, for example, tear-apart products that require sufficient strength to remain intact during manufacture and distribution, but that can be easily separated by the end user as needed. Another application of the present invention is to imprint a grooved design that can then be the beginning of areas that will easily fold into designs like boxes or corners. Other applications utilize the ability to impart a different stiffness in one direction versus another. Further, the grooves can be made to interdigitate with each other if the web is folded back upon itself. Formulation of the polymer may include tackifiers to allow the web to stick to itself upon opposing onto itself or onto another sheet. The increased surface area of the grooves can improve heat sealing of edges when the grooves recess into each other and are heated.

Nasal Dilators

Nasal dilators have provided innumerable people with relief from snoring or nasal congestion. Nasal dilators, such as those shown in U.S. Pat. Nos. 5,533,499, 5,706,800, and 7,114,495, typically include one or more resilient bands. When the resilient band is bent so that the ends of the band are moved closer together, the resilient band has a tendency to return to a planar state. When a nasal dilator is secured to a user's nose, the tendency of the resilient band to return to a planar state acts to prevent the outer wall tissue of the user's nasal passages from drawing in during breathing. In addition to a resilient band, nasal dilators often include additional flexible layers, in order to enhance the comfort and efficacy of the nasal dilators.

As discussed in U.S. Pat. No. 5,476,091, issued to Johnson, a flexible strip of material positioned between the resilient band and the user's skin spreads out delaminating forces resulting from the resiliency of the dilator that could otherwise cause the nasal dilator to inadvertently become detached from the user's skin. The separation of the nasal dilator from portions of the user's skin can cause itching sensations. Therefore, by spreading out the delaminating forces, the flexible strip of material can substantially eliminate itching sensations that would otherwise be felt by the user.

As described in U.S. Pat. No. 5,611,333, issued to Johnson, a nasal dilator may also include a flexible strip of top material, which covers the top of the resilient band. The flexible strip of top material may be included in order to help to prevent separation of the resilient band from the base material. The top material may also be included in order to increase the stiffness of the nasal dilator.

There is a continuing need for improved nasal dilators that are able to provide the force needed to lift and open the nasal passages, while being comfortable for extended, often overnight use, and that can be gently and easily removed from the user's nose.

Using the methodology of the present invention, it is possible to manufacture a nasal dilator comprising a material having specific flexural properties by imparting a particular set of grooves into the material. The method can use extrusion technology on plastic polymers or other materials to make a nasal dilator having the desired mono-axial flexural stiffness needed to effectively dilate the nasal passages.

In order to provide sufficient dilation, a nasal dilator is preferably able to lift the tissues of the nasal passages when the dilator is initially secured to the nose, and is preferably able to continue lifting the nasal tissues over a period of time, without significant discomfort to the user. At the end of the desired period of use, the nasal dilator is preferably easily removable from the user's nose, also without significant discomfort to the user.

A grooved nasal dilator in accordance with the present invention is preferably able to lift the lateral, lesser and greater alar cartilage structures of the nose, and preferably also facilitates the anterior and posterior dilator nares muscles of the nose. The grooved nasal dilator includes some type of engagement means, such as an adhesive, on the surface facing the user's skin. Preferably, the adhesive can removably adhere to the skin without causing skin irritation. In a preferred embodiment, the adhesive material is one that can absorb or transmit the moisture emanating up from the skin's surface. One example of such an adhesive includes hydrocolloid adhesives commonly used in ostomy bag adhesion or in wound care. Embedding the hydrocolloid into the grooves provides a larger repository for moisture accumulation without adding significant thickness or bulk to the overall profile of the nasal dilator. The grooved nasal dilator can remain in place over a period of time, without significant discomfort to the user, either while wearing the dilator or when removing the dilator.

In order to significantly reduce the outer wall tissue of a user's nasal passages from drawing in during breathing, the nasal dilator of the present invention utilizes a grooved material made with a certain stiffness, adhered directly to the nose. The resilience of the grooved material can reduce or eliminate the need for one or more resilient bands, such as the resilient bands of the nasal dilators described in U.S. Pat. Nos. 5,533, 499, 5,706,800, and 7,114,495. Therefore, if the grooved material of the present invention is used in a nasal dilator, a separate resilient band or bands may not be required.

If a separate resilient band is used in combination with the grooved material of the present invention, the stiffness of the grooved material may make it possible to reduce the size of the resilient band that is necessary to provide sufficient stabilization and lifting of nasal tissue. Therefore, when used with the grooved material, the resilient band may be much smaller, lighter, and less obtrusive than in previous nasal dilators.

Another advantage of the present invention is that it can simplify manufacturing by eliminating an entire component, namely, the resilient band, of a nasal dilator. Alternatively, if a resilient band is used in conjunction with the material of the present invention, a smaller, finer resilient band can be used, thereby providing a more fine-tuned, less obtrusive nasal dilator.

Figure 7A:
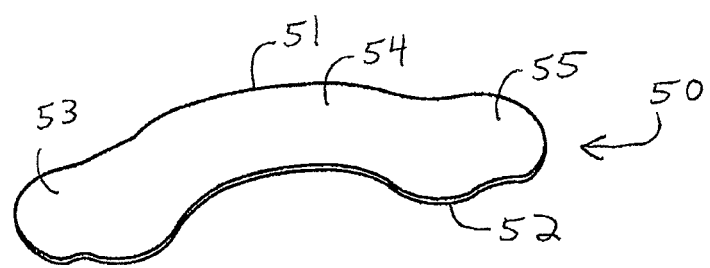
FIGS. 7a-b are views of an embodiment of a nasal dilator made in accordance with the present invention.
Figure 7B:
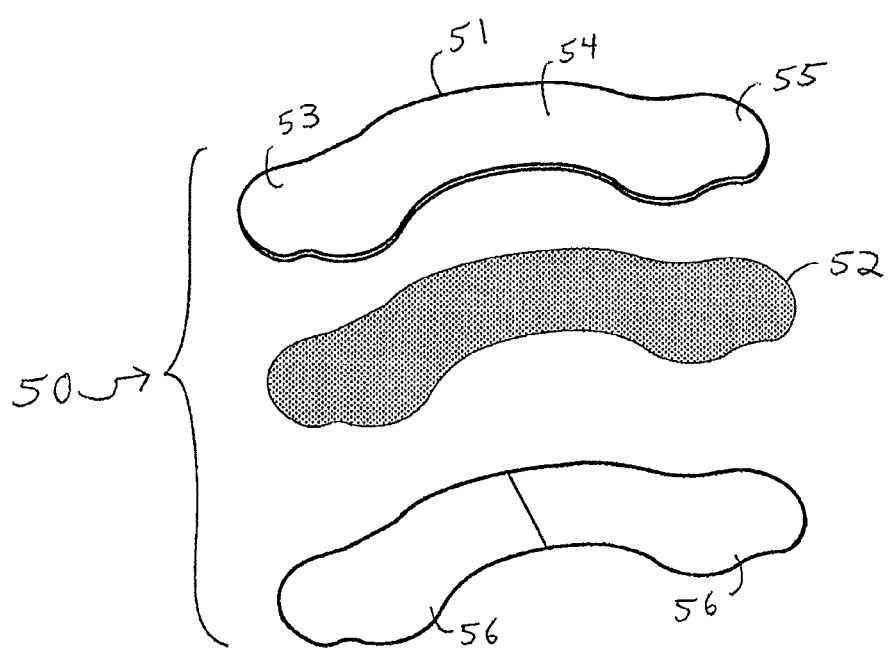

FIGS. 7a-b show an embodiment of a nasal dilator made in accordance with the present invention. FIG. 7a is a perspective view of the nasal dilator, and FIG. 7b is an exploded perspective view showing the components of the nasal dilator. In this embodiment, no separate resilient band is used. The nasal dilator 50 comprises a grooved material 51. The grooved material 51 includes an intermediate region 54 and end regions 53 and 55. The grooved material 51 is sized so that the intermediate region 54 is able to traverse the bridge of a user's nose, and the end regions 53 and 55 are able to contact the outer wall tissues of the user's nasal passages. A layer of a biocompatible adhesive substance 52 is disposed on one side of the grooved material 51. This adhesive secures the nasal dilator to the skin of the user during use.

When the grooved material 51 is bent so that the end regions 53 and 55 are moved closer together, the grooved material 51 has a tendency to return to a planar state. When the nasal dilator 50 is secured to a user's nose, the tendency of the grooved material 51 to return to a planar state acts to prevent the outer wall tissue of the user's nasal passages from drawing in during breathing.

The nasal dilator 50 may optionally include a release liner or liners 56 which are adhered to the grooved material 51 via the adhesive substance 52. If included, the release liner or liners are removed prior to use.

Figure 8:
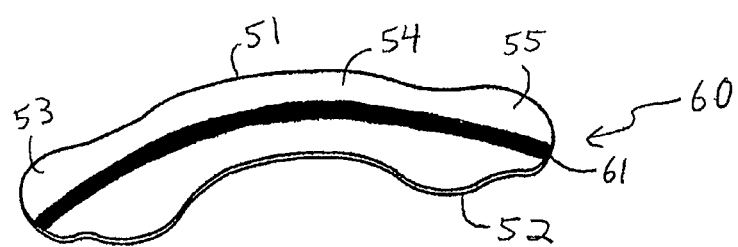
FIG. 8 is a view of another embodiment of a nasal dilator made in accordance with the present invention.

Another embodiment of a nasal dilator made in accordance with the present invention is shown in FIG. 8. This nasal dilator 60, like the nasal dilator 50 of FIG. 7, comprises a grooved material 51 and a biocompatible adhesive substance 52. The grooved material 51 is sized so that the intermediate region 54 is able to traverse the bridge of a user's nose, and the end regions 53 and 55 are able to contact the outer wall tissues of the user's nasal passages. The nasal dilator 60 may also include a release liner or liners which are adhered to the grooved material 51 via the adhesive 52.

The nasal dilator 60 also includes a resilient band 61, positioned on either side of the grooved material 51. In another embodiment, a plurality of resilient bands is used with the grooved material 51. When the nasal dilator 60 is bent so that the end regions 53 and 55 are moved closer together, both the grooved material 51 and the resilient band 61 have a tendency to return to a planar state. When the nasal dilator 60 is secured to a user's nose, the tendency of the grooved material 51 and the resilient band 61 to return to a planar state acts to prevent the outer wall tissue of the user's nasal passages from drawing in during breathing.

Figure 9A:
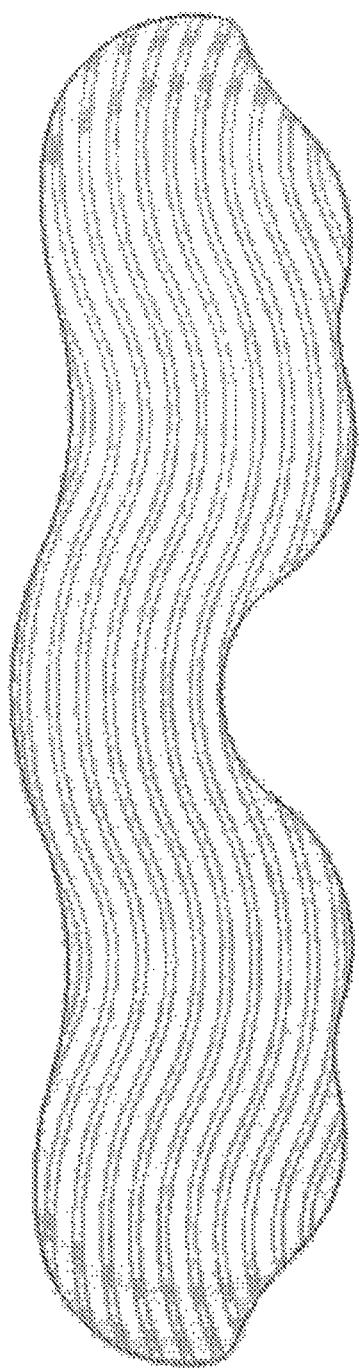
FIGS. 9a-c are views of various embodiments of a nasal dilator made in accordance with the present invention.
Figure 9B:
Figure 9C:
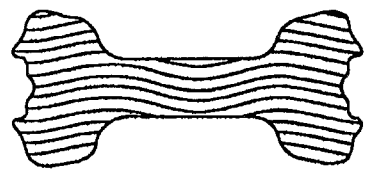

By using a grooved or etched polymer material as described above, nasal dilators of the present invention can be made very efficiently using extrusion techniques to impart the grooves to the material. Further embodiments of the nasal dilator in accordance with the present invention are shown in FIGS. 9*a-c*.

The dimensions of the grooves, along with the properties of the material, will determine the flexural stiffness of the extruded nasal dilator. By using the methodology of the present invention, the dimensions of the grooves can be selected to optimize the anisotropic flexural properties in the longitudinal direction, as well as the transverse direction.

The grooves can have a variable cross-section or thickness within the nasal dilator to provide for different stiffness or resiliency depending on the location of the grooves on the nasal dilator.

For example, looking at a side view of the dilator, the grooves may have ridges that are higher along the center portion of the dilator, and shorter along the edges of the dilator. Alternatively, there may be one or more grooves having a higher profile, separated by one or more grooves that are shorter, followed by another groove or grooves that are higher. In another embodiment, a grooved region, having one or more grooves, may be adjacent to a region that does not have grooves, or has a different profile imparted onto that region. In this way, the relative stiffness and flexibility of the material can be carefully controlled to provide the desired degree of resiliency, comfort and removability.

Figure 10A:
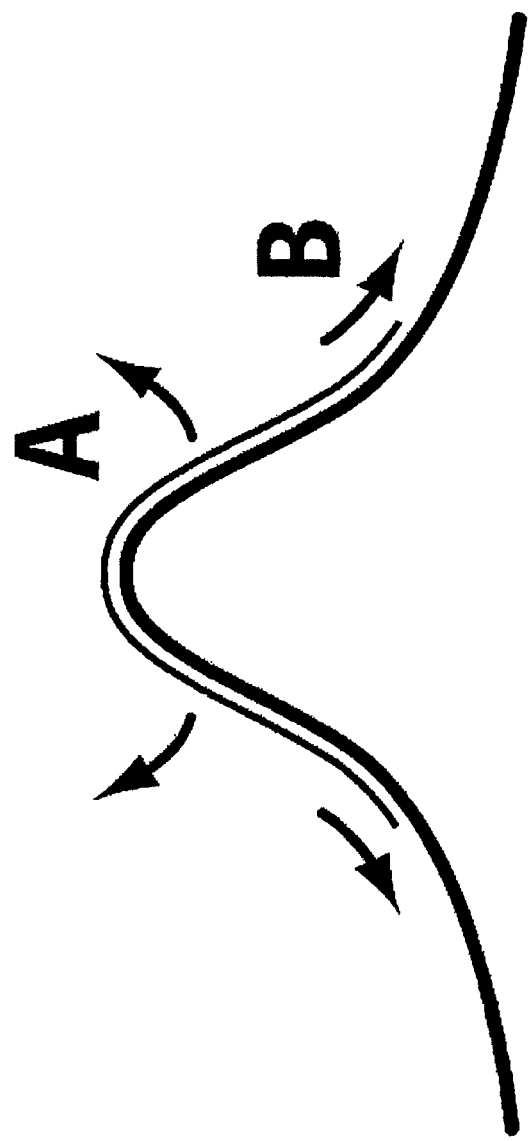
FIGS. 10a-c are diagrams of a nasal dilator of the present invention worn on the user's nose.
Figure 10B:
Figure 10C:

The nasal dilator may have any shape suitable for use on the nose or on the nasal passages. Preferably, the nasal dilator has a center region and two extending regions extending outwardly from the center region. By providing the desired resiliency to the nasal dilator, it is possible to convert the peel forces associated with the dilator in its latent, planar configuration to shear forces at the ends of the dilator when the extending regions are curved around the nose, as depicted in FIGS. 10*a-c*. The "A" arrows in FIG. 10*a* show the dilating force of the nasal dilator holding the nasal passages open, while the "B" arrows show the effects of shear force to keep the nasal dilator in place. This combination of forces provides the tension and lifting necessary to keep the nasal passages dilated during use. Preferably, the nasal dilator of the present invention provides between about 10 g to about 50 g of dilating force, more preferably, between about 12 g to about 40 g of dilating force, when the ends of the nasal dilator are positioned towards each other to be between about 1 to 1.5 inches apart. In one preferred embodiment, the nasal dilator of the present invention provides between about 14 g to about 30 g of dilating force, when the ends of the dilator are positioned to between about 1 to 1.2 inches apart during the course of use, which may vary from a few minutes to several hours, or preferably, overnight. Those skilled in the art will appreciate that the amount of force provided by the nasal dilator in use may deteriorate as the dilator is used, due to, among other things, relaxation of the dilator material and deterioration of the adhesive, so it is important to ensure that there is sufficient dilating force initially and during the course of use to keep the nasal passages open. It is preferred that the dilating force not deteriorate by more than about 20% over about an 8 hour time period. Yet another embodiment of a nasal dilator of the present invention provides for a greater dilator force initially with a rapid decline in lifting force over 8-12 hours. It has been found that PETG polymer is particularly preferred to maintain sufficient stiffness of the nasal dilator over time.

The shear force is a function of the type of adhesive used to secure the nasal dilator to the user's nose, and is therefore related to the amount of dilating force provided by the nasal dilator. Preferably, the shear force is sufficient to keep the nasal dilator in place during use, and can be easily overcome by the user when removal of the nasal dilator is desired.

The dilator may have any number of shapes, such as those shown in U.S. Pat. No. 6,029,658, 6,318,362, or 7,114,495, or as shown in the Figures.

The nasal dilator of the present invention may be symmetrical along its long axis, or it may be asymmetrical along its long axis. The asymmetrical long axis may facilitate proper positioning of the dilator, and may provide a better fit to the shape of the nose, thereby improving the dilation and comfort of the nasal dilator in use. Preferably, the nasal dilator is symmetrical along its short axis. The symmetry along the short axis provides substantially uniform dilating forces on both sides of the nose.

Figure 11:
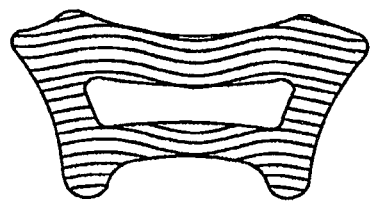
FIG. 11 is a view of another embodiment of the nasal dilator of the present invention.
Figure 12:
FIG. 12 is a view of another embodiment of the nasal dilator of the present invention.

In another embodiment of the present invention, the dilator made with the grooved material may have a center aperture or opening, an example of which is shown in FIG. 11. This center aperture may be of any size or shape, and may comprise a cut out portion or a narrow slit, as shown in FIG. 12.

The center aperture may include more than one aperture. The center aperture provides, among other things, an easy way for the user to center the dilator on his or her nose to assure proper placement for the most effective dilation. The center aperture or opening can be made by any conventional process, such as by die cutting the nasal dilator.

Figure 13:
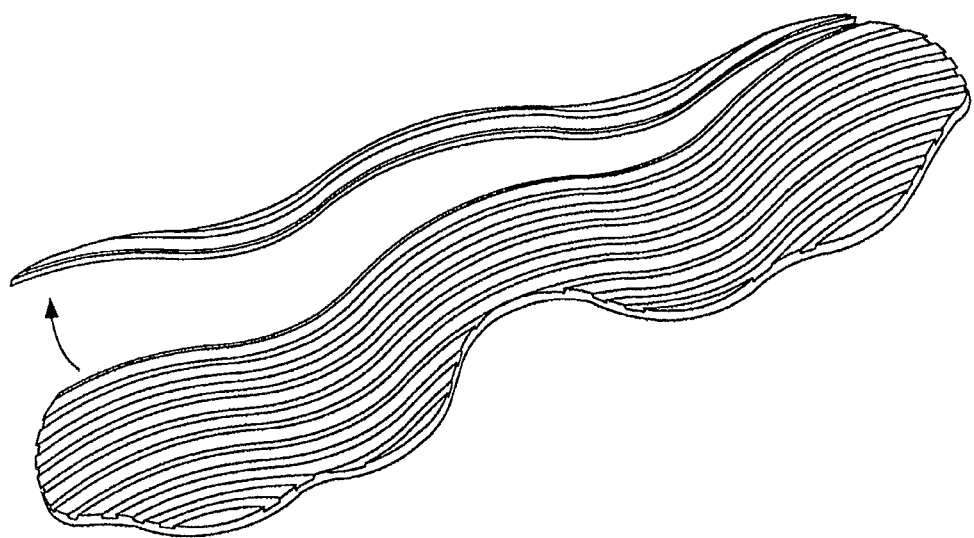
FIG. 13 is a view of another embodiment of the nasal dilator of the present invention.

The nasal dilator of the present invention may include a notch or a plurality of notches along the channel or channels of the material. By providing such notches, the size of the material used to make the nasal dilator can be easily laterally adjusted by removing one or more longitudinal groove portions, as shown in FIG. 13.

The stiffness of the grooved material of the nasal dilator can be further adjusted after the extrusion process. In one embodiment, the stiffness of the material on one or more peripheral edges may be reduced to make the dilator more comfortable and easier to remove by the user. The stiffness can be reduced by using various techniques, such as laser cutting, water jet cutting, ultrasonic cutting, electron beam cutting, mechanical abrasion, and the like to remove or thin out portions of the material as desired.

The nasal dilator of the present invention may include an additional component or components as described above. The additional component may be incorporated into the polymeric material before or after it is extruded.

For example, a mentholated nasal dilator can be made in accordance with the present invention by providing a grooved nasal dilator having a menthol fragrance delivery system incorporated with the dilator, either before or after extrusion. Examples of suitable fragrance or medication delivery systems are described in U.S. Pat. Nos. 5,706,800; 6,244,265; 6,276,360; 6,550,474; 6,769,428; 7,011,093; and 7,013,889, each of which is fully incorporated herein by reference.

The nasal dilator of the present invention can include features or elements associated with other nasal dilators, such as a material in contact with the user's nose under the nasal dilator, a cover, a full or partial adhesive void, a release liner or backing, and the like. Examples of such features and elements are described in U.S. Pat. Nos. 5,476,091; 5,533,499; 5,533,503; 5,549,103; 5,611,333; 5,653,224; and 6,318,362, each of which is fully incorporated herein by reference.

Flexural Stiffness Calculations for a Nasal Dilator

To optimize the flexural properties of the nasal dilator, calculations must be made based on the varying loads that are applied to the dilator. A nasal dilator typically has a downward load on each end, with an upward load in the center. Due to the deflection of about 45.degree. at each end, equations typically used in beam analysis must be used with care.

One can begin by using common beam equations to model the dilator because the loading herein is not continuously vertical, but remains predominantly lateral. The mechanical design issues at the large flexural strains of this application are then material properties and the effects of the resulting axial loading. This axial compression will somewhat reduce the tensile loading in the upper and increase the compressive loading in the lower fibers of the dilator under load.

Modeling the dilator as a beam with a concentrated load, rather than a distributed load, will introduce errors in both the geometry of the deflection and the magnitude of the overall force needed at a particular deflection angle. For example, comparing the overall force as a point load at the end of a cantilevered beam to a uniformly distributed load along the beam results in the curvatures being to the third power in the former and the fourth power in the latter, as a function of distance from the support in the center. The deflection on the end of the former is about 2.7 times less than the latter.

While the equations are not generally valid for the large deflections of the ends of the dilator, one skilled in the art will appreciate the correlation of load modeling with actual loads and deflections. This load modeling and associated load testing method can serve as a means for determining the desired flexibility of the grooved nasal dilators of the present invention.

In addition to the location of the loading, the deflection of a beam, such as the nasal dilator, is generally related to four parameters:

Magnitude of the load
Cross-section of the beam
Elasticity of the material
Length of or distance along the beam Therefore, deflection at a point on a beam is usually characterized by an equation such as:

Deflection on the beam=(Load)×(measure of the cross-section)×(measure of the elasticity)×(measure related to position along the beam)

This can be represented as:

$$y = Px(1/I) \times (1/E) \times (\text{function of } x)$$

where P is the force, I is the moment of inertia (second moment) of the beam cross-section, E is the modulus of elasticity, and x is the distance from the support, with the loading geometry/distribution determining the particular function of x.

Once a dilator configuration is defined, the geometry value of I and the material property of E can be combined into "EI" (stiffness) or 1/(EI) (flexibility.) Then various loading scenarios can be evaluated.

For a cantilevered beam loaded laterally at its end (with small deflections), deflection at x is $$y = (Px^2)(1/EI)[(1/6)(3L - x)]$$

where L is the beam length
The maximum deflection is at the end (x=L):

$$y_{max} = (P)(1/EI)[(1/3)L^3]$$

Reference can be made to stiffness as:

$$\text{Stiffness} = (1/12)(F_m \times T^3)$$

$$\text{Or } EI = (1/12)(F_m \times T^3)$$

Again, the value of EI will change if the geometry of the beam cross-section changes. The above equation actually derives from a simple rectangular beam cross-section, which has an I value of:

$$I = (1/12) \times b \times h^3$$

where b is the lateral base of the rectangular cross-section and h is the height of the cross-section.

In the abbreviated equation above [Stiffness=$(1/12)(F_m \times T^3)$], $F_m$ is actually (E×b), and T is h.

Calculation of Load on a Beam

Figure 14:
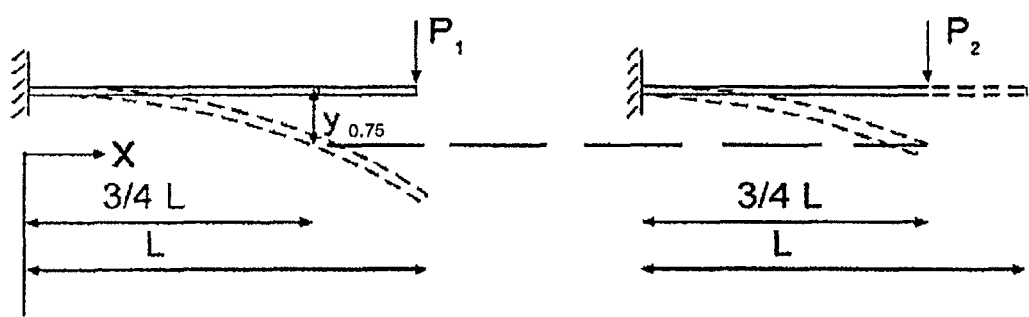
FIG. 14 is a diagram illustrating variables used in the calculation of a point load on a beam.
Figure 15:
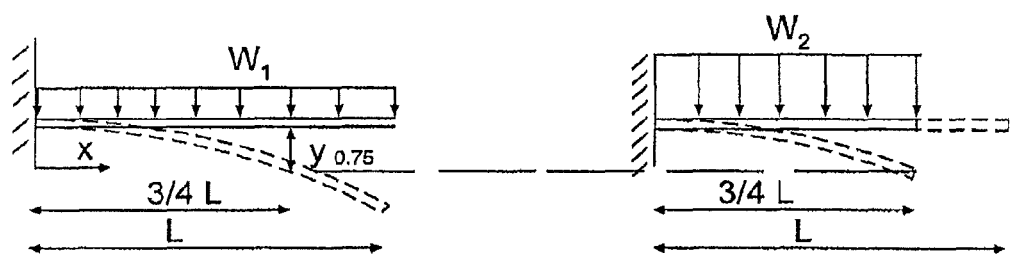
FIG. 15 is a diagram illustrating variables used in the calculation of a distributed load on a beam.

The following equations describe the calculations of a point or concentrated load on a beam, and a distributed load on a beam. As noted previously, while neither approach completely represents the actual load on a nasal dilator, one skilled in the art will recognize that models based on these approaches will be useful in determining the desired flexibility of the grooved nasal dilators of the present invention. FIG. 14 is a diagram illustrating variables x, y, L, $P_1$, and $P_2$ used in the calculation of a point load. FIG. 15 is a diagram illustrating variables x, y, L, $w_1$, and $w_2$ used in the calculation of a distributed load.

Calculation of a Point Load (P)

$$y = \frac{Px^2}{6EI}(3L-x) y_{max} = \frac{PL^3}{3EI}$$

to achieve the same deflection at $$x = \frac{3}{4}L: \frac{P_1\left(\frac{3}{4}L\right)^2}{6EI}\left(3L - \frac{3}{4}L\right) = \frac{P_2\left(\frac{3}{4}L\right)^3}{3EI}$$

$$\hookrightarrow P_2 = (1.5)P_1$$

Calculation of a Distributed Load (w)

$$y = \frac{Wx^2}{24EI}(x^2 + 6L^2 - 4Lx) y_{max} = \frac{wL^4}{8EI}$$

to achieve the same deflection at $$x = \left(\frac{3}{4}\right)L: \frac{W_1\left(\frac{3}{4}L\right)^2}{24EI}\left[\left(\frac{3}{4}L\right)^2 + 6L^2 - 4L = \left(\frac{3}{4}\right)L\right] = \frac{W_2\left(\frac{3}{4}L\right)^4}{8EI}$$

$$\hookrightarrow W_2 = (2.1)W_1$$

Calculation of Moment of Inertia (Second Moment, I)

The grooved nasal dilator's cross-section is not a simple, rectangular beam. The variations during design can significantly change the value of I, and thus the stiffness of the beam.

Figure 16:
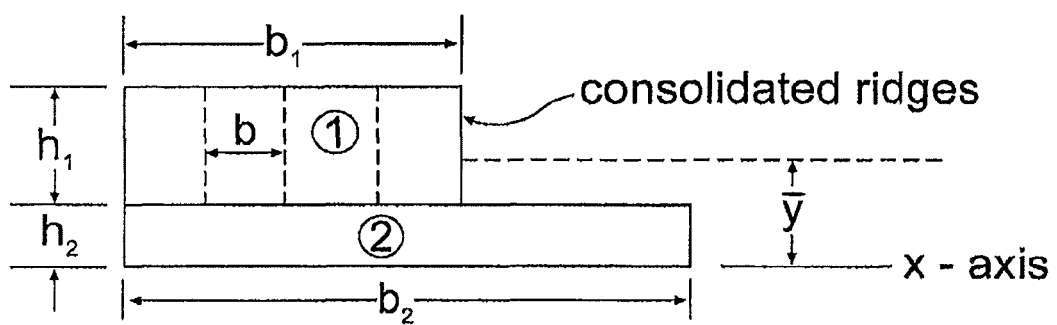
FIG. 16 is a diagram illustrating variables used in the calculation of a moment of inertia.

The total I of a particular design is calculated relative to the "neutral axis", which passes through the centroid of the composite cross-sectional area. The centroid location will vary with each design's cross-section. The following shows the equation for the distance (y) from the "base" of the product to the neutral axis. Also shown is the equation for determining the actual I, using this distance. FIG. 16 is a diagram illustrating variables $h_1$, $h_2$, b, $b_1$, and $b_2$ used in the calculation of a moment of inertia.

$$b_{1=}(n)(b) \text{ (total width of ridges)}$$

$$\sum(A_i \cdot y_i) = \left[\sum(A_i)\right]y$$

$$(h_1)(b_1)\left(h_2 + \left(\frac{h_1}{2}\right)\right) + (h_2)(b_2)\left(\frac{h_2}{2}\right) = [(h_1)(b_1) + (h_2)(b_2)]\bar{y}$$

$$y = \frac{(h_1)(b_1)(h_1 + 2h_2) + (h_2)^2(b_2)}{2[(h_1)(b_1) + (h_2)(b_2)]}$$

$$I_{x1} = (I_{x1})_1 + (I_{x1})_2$$

$$I_{x1}\left\{\left(\frac{1}{12}\right)(b_1)(h_1)^3 + (b_1)(h_1)\left[h_2 + \frac{(h_1)}{2} - y\right]^2\right\} +$$

$$\left\{\left(\frac{1}{12}\right)(b_2)(h_2)^3 + (b_2)(h_2)\left[y - \frac{(h_2)}{2} - y\right]^2\right\}$$

With these equations, one can calculate and compare the predicted stiffnesses of beams with any particular number of grooves and thicknesses or cross-sectional areas. If the material is defined, then comparing composite/total I values (or $I_{total}$ values) will be sufficient.

Example 1

Determination of Moment of Inertia (Second Moment) of the Cross-Sectional Area of a Grooved Nasal Dilator Using the equations above, the values of the nasal dilator configuration shown in FIG. 9a yields the values shown in Table I:

TABLE I

| L mm | $b_1$ mm | $h_1$ mm | $b_2$ mm | $h_2$ mm | $\bar{y}$ mm | $I_1$ mm$^4$ | $\Delta I_1$ mm$^4$ | $I_2$ mm$^4$ | $\Delta I_2$ mm$^4$ | $I_{total}$ mm$^4$ | $P_{test}$ Actual gm |
|---|---|---|---|---|---|---|---|---|---|---|---|
| 60 | 3.34 | 0.216 | 10.00 | 0.254 | 0.179 | 0.0028 | 0.0174 | 0.0137 | 0.0069 | 0.0408 | 64.0 |

The loading goal for a nasal dilator having a length of 46 mm is about 27 grams. The proportional $I_{total}$ to achieve this on a nasal dilator having a length of 46 mm is about 0.0171 mm$^4$.

Table II shows some calculated values. The first row represents a ridge height, English units, of 0.0012 inch and a base or valley thickness of 0.0035 inch. The second row shows a trial reduction of the grooves from 33% of the width to 30%. The third row shows instead a reduction of the ridge height from 0.012 inch to 0.0105 inch. Since neither resulted in an $I_{total}$ near 0.171 mm$^4$, both changes were employed, yielding $I_{total}$ of 0.0173 in$^4$. The proportional load predicted on a nasal dilator having a length of 46 mm with this $I_{total}$ is about 27.2 grams.

TABLE II

| L mm | $b_1$ mm | $h_1$ mm | $b_2$ mm | $h_2$ mm | $\bar{y}$ mm | $I_1$ mm$^4$ | $\Delta I_1$ mm$^4$ | $I_2$ mm$^4$ | $\Delta I_2$ mm$^4$ | $I_{total}$ mm | $P_{test}$ Predicted gm |
|---|---|---|---|---|---|---|---|---|---|---|---|
| 46 | 3.34 | 0.305 | 10.00 | 0.089 | 0.150 | 0.008 | 0.009 | 0.0005 | 0.010 | 0.0271 | 42.6 |
| 46 | 3.00 | 0.305 | 10.00 | 0.089 | 0.144 | 0.007 | 0.008 | 0.0006 | 0.009 | 0.0244 | 38.3 |
| 46 | 3.34 | 0.267 | 10.00 | 0.089 | 0.134 | 0.005 | 0.006 | 0.0006 | 0.007 | 0.0192 | 30.2 |
| 46 | 3.00 | 0.267 | 10.00 | 0.089 | 0.129 | 0.005 | 0.006 | 0.0006 | 0.006 | 0.0173 | 27.2 |

There are many configurations (b's and h's) that can yield the desired I. This is one example of the iterative approach to finding a configuration that also meets other design and processing criteria.

In the embodiment of the present invention shown in FIG. 9a, the total thickness=$R_0+R_i$, where $R_0$ is the thickness of the base or valley of the groove, and $R_i$ is the thickness of the ridge of the groove. The valley width is defined in this embodiment to be about half the width of the ridges. The stiffness of the nasal dilator will be an addition of the component related to $R_0$ plus the component related to $R_i$. The base or valley width can be defined simply as the entire width of the lifting portion of the bracket.

The polymer material can be extruded as shown in FIG. 6a at a temperature of about 400° F., under a pressured nip roller, at a rate of about 25 feet/minute, then laminated with an adhesive material and a release layer as shown in FIG. 6b, at a temperature ranging from about 180° F. to 215° F., through a pressured nip roller, and at a rate of 25 feet/minute. After the laminated material leaves the extruder, it can be subjected to further processing, such as laser cutting, to form nasal dilators having the desired size and shape.

Preferably, the adhesive material is applied to the grooved surface of the material, so that adhesive can be applied within each groove. In one embodiment, the adhesive is applied to partially or substantially fill the grooves. In another embodiment, the adhesive is applied to only the top portions of the grooves.

As described herein, any suitable adhesive material may be used, such as acrylate-based adhesives or hydrocolloid adhesives. The amount of adhesive material applied will vary depending on the dimensions of the grooves and the type of adhesive material or materials used. For example, in one embodiment of a nasal dilator of the present invention, each groove is filled with about a 10 mil thick layer of adhesive, such as a rubber-based adhesive.

For a nasal dilators without a central opening, such as those shown in FIGS. 9a-c, preferably the length of the nasal dilator may range from between about 35 mm to about 60 mm, the width may range from about 10 mm to about 25 mm, the valley thickness may range from between about 3 mil to about 10 mil, and the ridge thickness may range from between about 8 mil to about 15 mil. In one preferred embodiment, the ridge thickness was about 14 mil, the valley thickness was about 3.5 mil, and the total thickness of the ridge plus the valley thicknesses was about 17.5 mil.

For nasal dilators with a central opening, and two lifting brackets, such as the nasal dilator shown in FIG. 11, the length may range from between about 40 mm to about 55 mm and the width may range from between about 25 mm to 30 mm, with the same ranges for the ridge and valley thicknesses described above.

As noted previously, the valley width is preferably about half of the ridge width. In one preferred embodiment, the ridge width and valley width each range from between about 0.5 mm to about 1.0 mm, although these values can change depending in part on the material being used and the desired stiffness of the extruded material. The ratio of valley width to ridge width may also vary, again, depending in part on the material used and the desired stiffness of the extruded material.

The grooved and laminated material for nasal dilators can be laser cut to provide nasal dilators having the desired size and shape. In addition, the edges of the cut material can be further processed to increase comfort and ease of use. Preferably, the stiffness of the edges is reduced by about 85% compared to the center portions of the material. In one preferred embodiment, the edges are reduced from 14 mil to 4 mil in thickness. In another preferred embodiment, the edges are reduced to about 2 mil to 3 mil in thickness.

The size, shape and stiffness of nasal dilators made as described above were suitable for comfortably lifting the tissues of the nasal passages for a desired period of time.

In another embodiment of a nasal dilator made in accordance with the present invention, rather than embedding adhesive material within each groove, a thin layer of adhesive is applied to the top of one or more ridges of the grooves. For example, one or more ridges can be coated with about a 0.5 mil thick layer of adhesive, such as an acrylate adhesive.

In this embodiment of a nasal dilator, because only the top of the ridge or ridges is in contact with and adhered to the user's skin, there will be a partially or substantially open channel between the groove and the user's skin, running longitudinally from one end of the dilator to the other, or from one end of the dilator to another location along the length of the dilator. The plurality of channels can alternatively crisscross to form a "dimpling" to the surface of the nasal dilator in contact with the user's skin. The adhesive is applied to only the top most "islands" or ridge junctions created by the crisscrossing channels.

The channel or plurality of channels permit gases, fluids or liquids, such as water, air, oil or perspiration, to enter or collect in the channel, under the nasal dilator. The channel or channels may therefore increase the user's comfort when wearing the nasal dilator by permitting the evaporation of accumulated body moisture out of the channels, or by providing a reservoir in which oil secreted from the user's skin can accumulate away from the skin's surface.

The channel or channels may additionally or alternatively make it easier to remove the nasal dilator, by permitting water to enter the channel or channels when the user applies water to his or her face to remove the nasal dilator. When water is flushed into the space within the channels under the nasal dilator, air can then escape from under the dilator in any direction as determined by the position of the channel or channels. The channel or channels help facilitate the removal of the nasal dilator by increasing the surface area under the nasal dilator that can be put in contact with water, thereby deactivating more of the adhesive in contact with the user's skin.

Packaging Materials

As described above, the present invention can be used to make packaging materials having improved handling properties. Specifically, it has been surprisingly discovered that by using the grooved material described herein, package opening regions can be created which require far less force to tear apart, and have no sharp or irregular edges, as commonly associated with plastic packaging, such as PVC clamshell packaging. In one embodiment, it is possible to reduce the force required to open the package by about 98% using the grooved material of the present invention.

Figure 17:
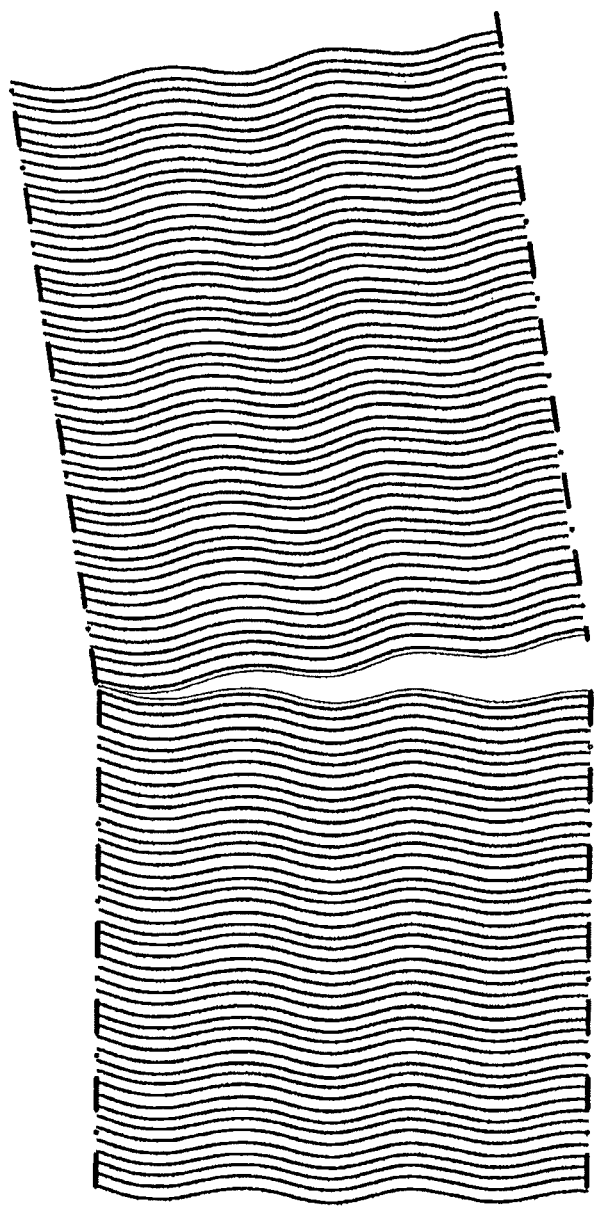
FIG. 17 is a view of the grooved material separated along a groove.

The use of the grooved material as packaging can reduce the amount of resin needed, in some cases by about 15% to 20%, thereby reducing the cost and environmental impact of the packaging. The grooved material surprisingly does not exhibit a reduction in blunt force resistance under compression as compared to the same material in an ungrooved form. The grooved material maintains its resistance to tearing across the grooves as compared to the ungrooved material, but by initiating a cut or notch along a groove, the grooved material can be torn apart safely and easily, as shown in FIG. 17.

The grooved material may also provide regions of improved flexibility, making it suitable for bending into a box or other shape.

The grooved material can be made more optically appealing, comparable to a "clear plastic" packaging material, by varying the cross-sectional appearance of the grooves, such as a "V" shaped groove rather than a squared groove. In addition, it may be possible to polish the etched roller's channel to remove the acid etch matte finish in the grooves to reduce the opacity of the material, making it more transparent.

The channels or valleys in the grooved material can be used to transfer fluids or gases into or out of a package or from one end of the channel to the other.

The grooved material can be covered with a second film to create a fluted plastic "cardboard-like" material for greater rigidity. Open-ended fluted corrugated plastic has not been readily used in medical or agricultural applications due to the possibility of entrapping dirt or unwanted biological materials. The present invention can be used to imprint closed, transverse brackets into the web of material, in either a repeatable design or at random. These closed brackets function by closing off the fluted ends of the material, thereby eliminating the possibility of dirt or biological contamination.

Medical Uses

In addition to the medical packaging application described above, the grooved material of the present invention can be used as a supportive material in a cast or splint. The grooved material can be rolled around an extremity, then scored and cut to size. The ability of the material to be easily cut to size makes it suitable for use in triage, emergency or battlefield situations. Again tackifiers such as polybutene, can be added to allow the material to attach to itself after reflecting back over a digit or extremity and on to itself. The channel or channels created by the grooves permit the transmission of gases, fluids or liquids, such as water, blood, oil or perspiration, into or out from under the grooved material in contact with the wearer's skin.

Construction Materials

The grooved material of the present invention can be used to make construction materials, such as flooring, or as sheeting material for containment purposes.

One example of a type of flooring that can be made with the present invention is linoleum flooring. The grooves can be made into flutes (as mentioned above) in the material and can facilitate the passage of warmed liquids or gases to heat or cool flooring.

Current containment sheeting is very difficult to handle on site to position and size appropriately. The grooved material of the present invention permits unrolling the material along a surface, such as a wall or floor, to the desired size, then scoring and tearing the material along a groove.

The grooved material can include polybutene or similar adhesive to provide the material with a degree of tackiness or stickiness to facilitate its use.

Anti-microbial agents, such as anti-fungal or anti-spore treatment compounds, can be added to the web of material for use in situations in which moisture damage needs to be controlled. Other applications include the use of the grooved material to set up or contain designated "clean rooms".

Insect repellant agents can be added to the material for use in infested areas, either as temporary shelter, or as part of a permanent structure. Examples include DEET, Permethrin, or Picaridin.

Although the foregoing examples and embodiments describe various aspects and applications, they are not intended to limit the scope of the present invention, which is set forth in the following claims.

What is claimed:

1. A medical device comprising:
a one-piece band of base material having opposite first and second side surfaces, the one-piece band resiliently biasing itself into a planar state; and
an adhesive material coupled to at least a portion of the first side surface of the one-piece band for temporarily adhesively securing the one-piece band to a user's skin, wherein the one-piece band comprises:
a longitudinal axis and a lateral axis that intersects the longitudinal axis,
first and second lateral portions disposed on opposite sides of the lateral axis,
the first and second lateral portions being mirror images of each other such that the one-piece band is symmetrical relative to the lateral axis, each of the first and second lateral portions including a central portion and first and second extending portions spaced apart from each other on opposite sides of the longitudinal axis by a cut-out portion and extending away from the central portion, each of the first and second extending portions including a perimeter edge defining at least a portion of a perimeter edge of the medical device,
the first and second lateral portions further being contiguous with each other and having substantially continuous stiffness along the entirety of the longitudinal axis.

2. The medical device of claim 1, wherein the first and second extending portions define first and second corner zones of the one-piece band, respectively, the first and second corner zones disposed on opposite sides of the longitudinal axis and including at least one rounded corner.

3. The medical device of claim 1, wherein the one-piece band includes first and second inwardly curved longitudinal edges disposed on opposite sides of the longitudinal axis.

4. The medical device of claim 1, wherein the longitudinal axis of the one-piece band is longer than the lateral axis.

5. The medical device of claim 1, further comprising a release liner removably coupled to the adhesive material, the release liner adapted to be removed prior to securing the medical device to the user's skin.

6. The medical device of claim 1, wherein the one-piece band comprises at least one of the following materials: a thermoplastic polymeric material, an acrylonitrile-butadienestyrene (ABS), a polyethylene, a high density polyethylene (HDPE), a low density polyethylene (LDPE), a high molecular weight polyethylene (HMWPE), a polypropylene, a polyester, a polyethylene terephthalate (PET), a glycolised polyethylene terephthalate (PETG), a polystyrene, a polyurethane, a vinyl, a linoleum, a rubber compound, an acrylic, a nylon compound, a corn derivative, a biodegradable resin, a polylactic acid, and a polyhydroxyalkanoate.

7. The medical device of claim 1, wherein the one-piece band is grooved material.

8. The medical device of claim 1, wherein the adhesive material covers the entirety of the first side surface of the one-piece band.

9. The medical device of claim 1, wherein the cut-out portion is surrounded by the one-piece band of base material on all sides.

10. A medical device comprising:
   a one-piece band of base material having opposite first and second side surfaces, the one-piece band resiliently biasing itself into a planar state; and
   an adhesive material coupled to at least a portion of the first side surface of the one-piece band for temporarily adhesively securing the one-piece band to a user's skin,
   wherein the one-piece band comprises:
   a longitudinal axis and a lateral axis that intersects the longitudinal axis,
   first and second lateral portions disposed on opposite sides of the lateral axis,
   the first and second lateral portions being mirror images of each other such that the one-piece band is symmetrical relative to the lateral axis,
   the first and second lateral portions further being contiguous with each other and having substantially continuous stiffness along the entirety of the longitudinal axis,
   each of the first and second lateral portions including a central portion and first and second extending portions spaced apart from each other on opposite sides of the longitudinal axis by a cut-out portion and extending away from the central portion,
   each of the first and second extending portions including a perimeter edge defining at least a portion of a perimeter edge of the medical device,
   wherein the first and second extending portions define first and second corner zones of the one-piece band, respectively, the first and second corner zones disposed on opposite sides of the longitudinal axis and including at least one rounded corner, and
   wherein the one-piece band includes first and second inwardly curved longitudinal edges disposed on opposite sides of the longitudinal axis.

11. The medical device of claim 10, wherein the longitudinal axis of the one-piece band is longer than the lateral axis.

12. The medical device of claim 10, further comprising a release liner removably coupled to the adhesive material, the release liner adapted to be removed prior to securing the medical device to the user's skin.

13. The medical device of claim 10, wherein the one-piece band comprises at least one of the following materials: a thermoplastic polymeric material, an acrylonitrile-butadiene-styrene (ABS), a polyethylene, a high density polyethylene (HDPE), a low density polyethylene (LDPE), a high molecular weight polyethylene (HMWPE), a polypropylene, a polyester, a polyethylene terephthalate (PET), a glycolised polyethylene terephthalate (PETG), a polystyrene, a polyurethane, a vinyl, a linoleum, a rubber compound, an acrylic, a nylon compound, a corn derivative, a biodegradable resin, a polylactic acid, and a polyhydroxyalkanoate.

14. The medical device of claim 10, wherein the one-piece band is grooved material.

15. The medical device of claim 10, wherein the adhesive material covers the entirety of the first side surface of the one-piece band.

16. The medical device of claim 10, wherein the cut-out portion is surrounded by the one-piece band of base material on all sides.

* * * * *

UNITED STATES PATENT AND TRADEMARK OFFICE
CERTIFICATE OF CORRECTION

| | | |
|---|---|---|
| PATENT NO. | : 8,834,514 B2 | Page 1 of 1 |
| APPLICATION NO. | : 13/894941 | |
| DATED | : September 16, 2014 | |
| INVENTOR(S) | : David William Smith | |

It is certified that error appears in the above-identified patent and that said Letters Patent is hereby corrected as shown below:

On the Title Page:

Item (71), line 1, "Richmomd," should be -- Richmond, --.

Signed and Sealed this
Third Day of November, 2015

Michelle K. Lee
*Director of the United States Patent and Trademark Office*